(12) United States Patent
Mack et al.

(10) Patent No.: US 8,795,656 B2
(45) Date of Patent: Aug. 5, 2014

(54) METHODS OF TREATING RHEUMATOID ARTHRITIS BY ADMINISTERING AN ANTI-IL3 ANTIBODY

(75) Inventors: Matthias Mack, Regensburg (DE); Hilke Brühl, Regensburg (DE)

(73) Assignee: Klinikum der Universitat Regensburg, Regensburg (DE)

( * ) Notice: Subject to any disclaimer, the term of this patent is extended or adjusted under 35 U.S.C. 154(b) by 42 days.

(21) Appl. No.: 13/132,754

(22) PCT Filed: Dec. 4, 2009

(86) PCT No.: PCT/EP2009/008703
§ 371 (c)(1),
(2), (4) Date: Aug. 24, 2011

(87) PCT Pub. No.: WO2010/063488
PCT Pub. Date: Jun. 10, 2010

(65) Prior Publication Data
US 2012/0039872 A1    Feb. 16, 2012

(30) Foreign Application Priority Data
Dec. 4, 2008  (EP) .................................. 08021114

(51) Int. Cl.
*A61K 39/395* (2006.01)
*A61K 38/00* (2006.01)
*A61K 39/00* (2006.01)

(52) U.S. Cl.
CPC ........... *A61K 38/00* (2013.01); *A61K 2039/505* (2013.01)
USPC .................. 424/130.1; 424/133.1; 424/141.1; 424/145.1; 514/16.6

(58) Field of Classification Search
CPC .................... A61K 2039/505; A61K 38/00
USPC ..................... 424/130.1, 133.1, 141.1, 145.1; 514/16.6
See application file for complete search history.

(56) References Cited

U.S. PATENT DOCUMENTS

| 5,530,101 | A | * | 6/1996 | Queen et al. | 530/387.3 |
| 5,888,510 | A | * | 3/1999 | Kishimoto et al. | 424/141.1 |
| 2007/0110746 | A1 | | 5/2007 | Chung | |

FOREIGN PATENT DOCUMENTS

| EP | 1980855 A1 | 10/2008 |
| WO | WO0009561 A1 | 2/2000 |
| WO | WO0047620 A1 | 8/2000 |
| WO | WO2005069933 A2 | 8/2005 |

OTHER PUBLICATIONS

Abdollahi-Roodsaz et al., Inhibition of Toll-like receptor 4 breaks the inflammatory loop in autoimmune destructive arthritis, Arthritis Rheum., 56(9):2957-2967 (2007).

Abrams et al., Development of rat anti-mouse interleukin 3 monoclonal antibodies which neutralize bioactivity in vitro, J. Immunol., 140(1):131-137 (1988).

Alvaro-Gracia et al., Cytokines in chronic inflammatory arthritis. V. Mutual antagonism between interferon-gamma and tumor necrosis factor-alpha on HLA-OR expression, proliferation, collagenase production, and granulocyte macrophage colony-stimulating factor production by rheumatoid arthritis synoviocytes, J. Clin. Invest., 86(6):1790-1798 (1990).

Barton et al., IL-3 induces differentiation of bone marrow precursor cells to osteoclast-like cells, J. Immunol., 143 (10):3211-3216 (1989).

Brühl et al., Targeting of Gr-1+,CCR2+ monocytes in collagen-induced arthritis, Arthritis Rheum., 56(9):2975-85 (2007).

Brühl et al., Dual role of CCR2 during initiation and progression of collagen-induced arthritis: evidence for regulatory activity of CCR2+ T cells, J. Immunol., 172(2):890-898 (2004).

Buelens et al., Interleukin-3 and interferon cooperate to induce differentiation of monocytes into dendritic cells with potent helper T-cell stimulatory properties, Blood, 99(3):993-998 (2002).

Denzel et al., Basophils enhance immunological memory responses, Nat. Immunol., 9(7):733-42 (2008).

Dvorak et al., Effects of interleukin-3 with or without the c-kit ligand, stem cell factor, on the survival and cytoplasmic granule formation of mouse basophils and mast cells in vitro, Am. J. Pathol., 144(1):160-170 (1994).

Ebner et al., A novel role for IL-3: human monocytes cultured in the presence of IL-3 and IL-4 differentiate into dendritic cells that produce less IL-12 and shift Th cell responses toward a Th2 cytokine pattern, J. Immunol., 168 (12):6199-6207 (2002).

Ellington et al., In vitro selection of RNA molecules that bind specific ligands, Nature, 346:818-822 (1990).

Emanuel et al., Specific inhibition of interleukin 3 bioactivity by a monoclonal antibody reactive with hematopoietic progenitor cells, Proc. Natl. Acad. Sci. USA, 87(12):4449-4452 (1990).

Firestein et al., Cytokines in chronic inflammatory arthritis. I. Failure to detect T cell lymphokines (interleukin 2 and interleukin 3) and presence of macrophage colonystimulating factor (CSF-1) and a novel mast cell growth factor in rheumatoid synovitis, J. Exp. Med., 168(5):1573-1586 (1988).

(Continued)

*Primary Examiner* — Prema Mertz
(74) *Attorney, Agent, or Firm* — Kagan Binder, PLLC

(57) ABSTRACT

The use of an IL-3 inhibitor for prophylactic treatment of rheumatoid arthritis, for treatment of rheumatoid arthritis in an early stage, during early phases of exacerbation, or as maintenance therapy to prevent disease flares or disease progression in a subject is described.

13 Claims, 7 Drawing Sheets

(56) References Cited

OTHER PUBLICATIONS

Figure 1:
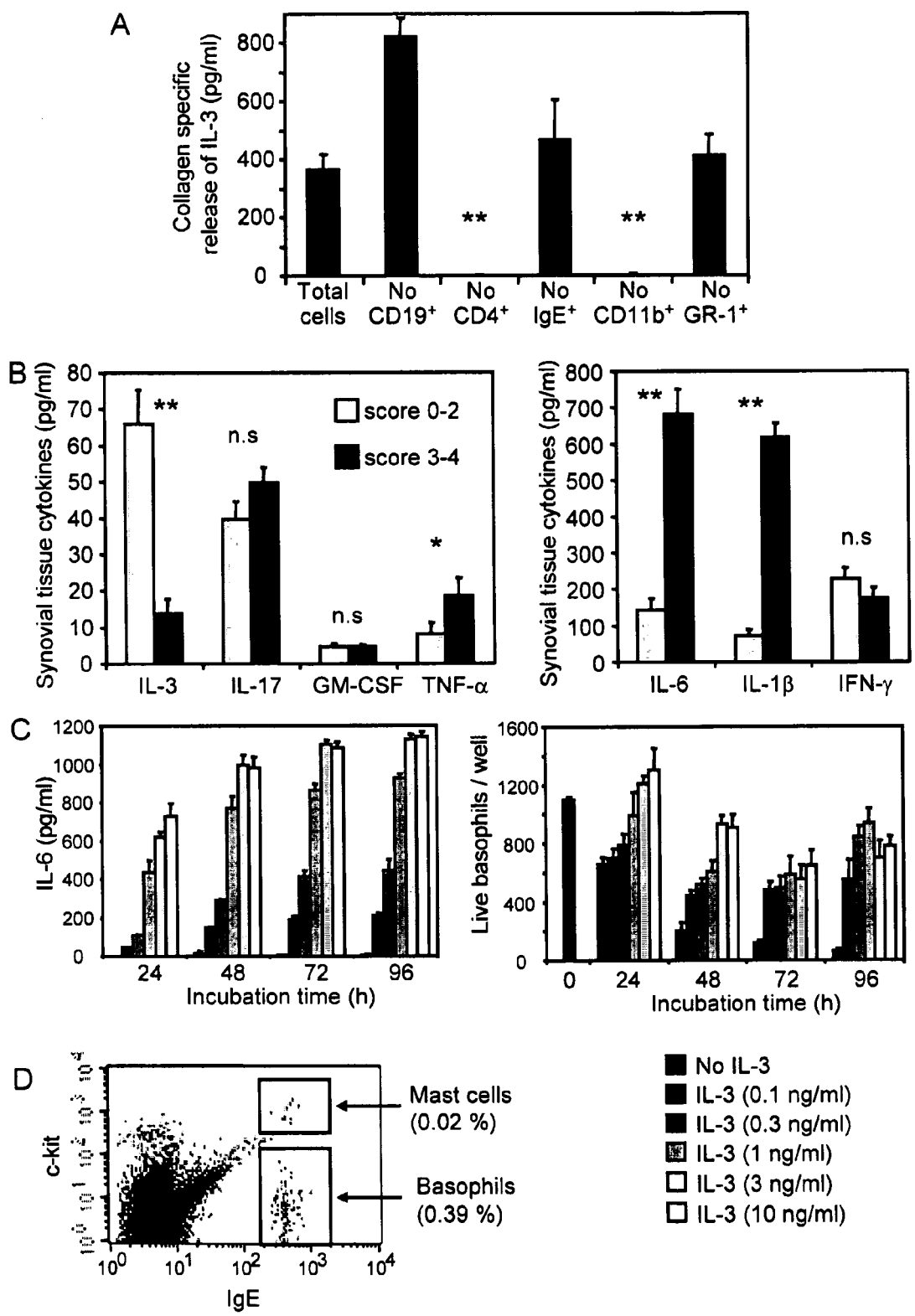

Frendl et al., Regulation of macrophage activation by IL-3. II. IL-3 and lipopolysaccharide act synergistically in the regulation of IL-1 expression, J. Immunol., 144(9):3400-3410 (1990).
Frendl et al., Regulation of macrophage activation by IL-3. I. IL-3 functions as a macrophage-activating factor with unique properties, inducing Ia and lymphocyte function-associated antigen-1 but not cytotoxicity, J. Immunol., 144 (9):3392-3399 (1990).
Haak-Frendscho et al., Human recombinant granulocyte-macrophage colony-stimulating factor and interleukin 3 cause basophil histamine release, J. Clin. Invest., 82(1):17-20 (1988).
Hara et al., Two distinct functional high affinity receptors for mouse interleukin-3 (IL-3), Embo J., 11(5):1875-1884 (1992).
Hawwari et al., The human IL-3 locus is regulated cooperatively by two NFAT-dependent enhancers that have distinct tissue-specific activities, J. Immunol., 169(4):1876-86 (2002).
Ihle et al., Biologic properties of homogeneous interleukin 3. I. Demonstration of WEHI-3 growth factor activity, mast cell growth factor activity, p cell-stimulating factor activity, colony-stimulating factor activity, and histamine-producing cell stimulating factor activity, J. Immunol., 131(1):282-287 (1983).
International Search Report for Application No. PCT/E2009/008703 dated Mar. 10, 2010.
Kirshenbaum et al., IL-3-dependent growth of basophil-like cells and mastlike cells from human bone marrow, J. Immunol., 142(7):2424-2429 (1989).
Kitamura et al., Establishment and characterization of a unique human cell line that proliferates dependently on GM-CSF, IL-3, or erythropoietin, J. Cell Physiol., 140(2):323-334 (1989).
Klussmann et al., Mirror-image RNA that binds D-adenosine, Nat. Biotechnol., 14:1112-1115 (1996).
Kohler et al., Continuous cultures of fused cells secreting antibody of predefined specificity, Nature, 256:495 (1975).
Kurimoto et al., Interleukin 3-dependent mediator release in basophils triggered by C5a, J. Exp. Med., 170 (2):467-79 (1989).
Lantz et al., Role for interleukin-3 in mast-cell and basophil development and in immunity to parasites, Nature, 392 (6671):90-93 (1998).
Lee et al., Mast cells: a cellular link between autoantibodies and inflammatory arthritis, Science, 297(5587):1689-92 (2002).
LeGros et al., IL-3 promotes production of IL-4 by splenic non-B, non-T cells in response to FC receptor cross-linkage, linkage, J. Immunol., 145(8):2500-2506 (1990).
Lokker et al., Mapping the epitopes of neutralizing anti-human IL-3 monoclonal antibodies. Implications for structure-activity relationship, J. Immunol., 146:893-898 (1991).
MacDonald et al., Recombinant IL-3 induces histamine release from human basophils, J. Immunol., 142 (10):3527-3532 (1989).

Miyajima et al., Cytokine receptors and signal transduction, Annu. Rev. Immunol., 10:295-331 (1992).
Morel et al., Identification of a novel protein capable of interacting with the IL-3 receptor, J. Immunol., 146 (7):2295-2304 (1991).
Nigrovic et al., Mast cells contribute to initiation of autoantibody-mediated arthritis via IL-1, Proc. Natl. Acad. Sci. USA, 104(7):2325-2330 (2007).
Stevens et al., Regulation of antibody isotype secretion by subsets of antigenspecific helper T cells, Nature, 334 (6179):255-258 (1988).
Sun et al., Monoclonal antibody 7G3 recognizes the N-terminal domain of the human interleukin-3 (IL-3) receptor alpha-chain and functions as a specific IL-3 receptor antagonist, Blood, 87(1):83-92 (1996).
Toyosaki-Maeda et al., Differentiation of monocytes into multinucleated giant bone-resorbing cells: two-step differentiation induced by nurse-like cells and cytokines, Arthritis Res., 3(5):306-310 (2001).
Tuerk et al., Systematic evolution of ligands by exponential enrichment: RNA ligands to bacteriophage T4 DNA polymerase, Science, 249:505-510 (1990).
Valent et al., Interleukin-3 is a differentiation factor for human basophils, Blood, 73(7):1763-1769 (1989).
Watanabe et al., Monoclonal antibody against the common beta subunit (beta c) of the human interleukin-3 (IL-3), IL-5, and granulocyte-macrophage colony-stimulating factor receptors shows upregulation of beta c by IL-1 and tumor necrosis factor-alpha, Blood, 80(9):2215-2220 (1992).
Written Opinion for Application No. PCT/E2009/008703 dated Jun. 7, 2011.
Yamada et al., Association between a single-nucleotide polymorphism in the promoter of the human interleukin-3 gene and rheumatoid arthritis in Japanese patients, and maxi mum-likelihood estimation of combinatorial effect that two genetic loci have on susceptibility to the disease, Am. J. Hum. Genet., 68(3):674-685 (2001).
Yoshimoto et al., IL-18, although antiallergic when administered with IL-12, stimulates IL-4 and histamine release by basophils, Proc. Natl. Acad. Sci. USA, 96(24)13962-13966 (1999).
Yoshino et al., Oral administration of lipopolysaccharide exacerbates collagen-induced arthritis in mice, J. Immunol., 163(6):3417-3422 (1999).
Zhou et al., Mast cell deficiency in Kit(W-sh) mice does not impair antibody-mediated arthritis, J. Exp. Med., 204 (12):2797-2802 (2007).
Bruhl et al., "Important Role of Interleukin-3 in the Early Phase of Collagen-Induced Arthritis," Arthritis & Rheumatism, vol. 60, No. 5, May 2009, pp. 1352-1361.
McInnes et al., "Cytokines in the pathogenesis of rheumatoid arthritis," Nature Reviews | Immunology, vol. 7, Jun. 2007, pp. 429-442.

* cited by examiner

METHODS OF TREATING RHEUMATOID ARTHRITIS BY ADMINISTERING AN ANTI-IL3 ANTIBODY

CROSS-REFERENCE TO RELATED APPLICATION

This application claims the benefit of European Patent Application No. 08021114.7 filed on Dec. 4, 2008, incorporated herein by reference in its entirety.

The present invention refers to IL-3 inhibitors used for prophylactic treatment of rheumatoid arthritis, early phases of exacerbation of rheumatoid arthritis and maintenance therapy of rheumatoid arthritis.

Rheumatoid arthritis (RA) is a chronic inflammatory and destructive joint disease that affects 0.5 to 1% of the population in the industrialized world and commonly leads to significant disability and a consequent reduction in quality of life. It is two to three times more frequent in women than in men and can start at any age, with a peak incidence between the fourth and sixth decade of life. Rheumatoid arthritis is associated with high costs and, if not treated appropriately, with a reduction in life expectancy. RA is characterized by a chronic inflammation of the membrane lining, the synovium, the joints and/or other organs. RA is a polyarthritis, in other of the hands, feet and knees but also the spine. An extraarticular involvement is another hallmark of RA and this can range from rheumatoid nodules to life threatening vasculitis. The inflammatory cells can invade and damage bone and cartilage. The joint involved can loose its shape and alignment, which results in a loss of movability. Patients with RA have pain, stiffness, redness and swelling in the joint and can have other systemic symptoms like fever. The disease progresses often discontinuously in the form of exacerbations or flare-ups, that is phases with high disease activity alternate with phases of low or moderate activity; the duration of the phases can differ significantly. The pathology of RA is not fully understood although it is postulated that it is caused by autoimmune reactions, i.e. a cascade of improper immunological reactions.

Generally cytokines play a role in inflammatory diseases. Irregular and/or abnormal inflammation is a major component of a wide range of human diseases, one of which is rheumatoid arthritis (RA).

One major subgroup of cytokines involved in inflammatory diseases is the interleukin family. Interleukins are involved in the T-cell activation cascade and the consequent inflammatory changes. They play a role in triggering a multiplicity of cell responses and in the polarisation into either $T_{H1}$ or $T_{H2}$ cells.

IL-3 is one member of the interleukin family and, together with IL-5 and GM-CSF, belongs to the family of hematopoietic cytokines with four short α-helical bundles. Each of these cytokines binds to a unique α-receptor subunit (e.g. IL-3Rα for IL-3). Signal transduction is mediated by a common β-receptor subunit (β-C) that is unable to bind any of the cytokines. In the mouse a second β-receptor subunit ($β_{IL-3}$) has been identified that associates exclusively with the IL-3Rα subunit. (2).

The T-cells infiltrating the synovial membrane in the rheumatic process are primarily CD4$^+$ memory cells which produce IL-2 and IFN-γ but also IL-3. However, little is known about the regulation of IL-3 secretion from T-cells. IL-3 contributes to the growth, differentiation and survival of CD34$^+$ hematopoietic progenitor cells. Although disruption of the IL-3 gene does not affect basal hematopoiesis it is necessary for supporting increased numbers of basophils and tissue mast cells during parasite infection. In vitro, IL-3 promotes the differentiation of basophils and mast cells from bone marrow cells (4-7). It has been described that IL-3 facilitates and induces histamine and IL-4 release by basophils (8-12). In monocytes/macrophages IL-3 upregulates MHC-II expression and enhances the LPS induced IL-1 secretion (13, 14). Together with IL-4 or IFN-β, IL-3 supports differentiation of monocytes into dendritic cells (15, 16). Also an induction of osteoclast like cells by IL-3 has been described (17, 18).

Until now little was known about the role of IL-3 in arthritis or rheumatoid arthritis. In an early study no IL-3 mRNA was detected in the synovium of patients with RA (19) and no effect of IL-3 on cultured fibroblasts like synoviocytes was observed (20). Nevertheless, a genetic analysis found an association between a single nucleotide polymorphism in the IL-3 promoter and rheumatoid arthritis (21).

It has been postulated or already shown that a number of cytokines are pro-inflammatory markers or anti-inflammatory mediators. The focus was on IL-6, IL-1β and TNFα as pro-inflammatory cytokines. In WO 2005/069933 it was indicated that those strategies that target a single pro-inflammatory cytokine for an anti-inflammatory therapy ignore a very important fact, which is that inflammatory-related diseases involve a sophisticated cytokine network system. It is outlined there that the functioning of the immune system is finely balanced by the activities of pro-inflammatory and anti-inflammatory mediators or cytokines and that the modulation of multiple cytokines is preferable over blocking only one particular pro-inflammatory cytokine. Therefore, WO 2005/069933 proposes to use specific compounds that inhibit a multiplicity of pro-inflammatory cytokines. This idea is also reflected in US 2007/0110746 where at least two substances capable of blocking the binding of MHC class II molecules should be used to block the binding of adhesion molecules and a receptor thereof in the treatment of inflammatory disorders.

The treatment of RA is difficult as this disease does respond mostly on medications that carry a high risk of adverse side effects. In the past two principal approaches for treatment have been made: symptomatic treatment with non-steroidal anti-inflammatory drugs (NSAIDs) and disease modifying anti-rheumatic drugs (DMARDs). NSAIDs, i.e. mainly anti-inflammatory and analgetic drugs, were used for treatment or at least pain release. They only interfere with a small segment of the inflammatory cascade, namely prostaglandin generation by cyclooxygenases (COXs), but do not interfere with underlying inflammatory events or retard joint destruction.

By contrast, DMARDs modify the disease process. Recently, within the group of DMARDs a new class of biological drugs has been developed based on a new understanding of the role of cytokines, particularly TNFα and IL-1, in the inflammatory process. Examples of DMARDs are methotrexate, leflunomide, or infliximab, i.e. anti-TNFα antibodies. Some drugs have been approved like anti-TNFα antibodies. However, it was found that again the side effects of TNFα- or IL-1 receptor antagonists are so severe that their use is restricted, although these drugs have been shown to interfere in the inflammatory process and can control the process.

All treatments proposed until today have the disadvantage of severe side effects. Therefore, it is still an objective to develop new drugs for the treatment of RA that are as effective as NSAIDs or DMARDs but have less side effects. Moreover it is an objective to provide medication for prophylactic treatment of RA, for treatment of RA in an early phase and/or to prevent exacerbations or flares.

These objectives have been solved by providing a new class for treatment of rheumatoid arthritis, particularly for treatment in an early stage and maintenance therapy, namely IL-3 inhibitors.

Thus, it is one aspect of the present invention to block or inactivate IL-3 in patients suffering from rheumatoid arthritis, particularly as prophylactic treatment, for treatment of RA in an early stage of exacerbations or phases of low to moderate disease activity.

In this description and the claims, reference will be made to a number of terms which shall be defined to have the following meanings:

The term "inhibiting IL-3" when used in this application shall refer to inhibiting the activity or function of this cytokine, particularly to inhibiting the binding of IL-3 to its receptor and/or inhibiting the signaling caused by that binding.

The term "IL-3 inhibitor" when used in this application refers to any substance that inhibits or blocks binding of IL-3 to its receptor and/or that interrupts the signaling cascade. An IL-3 inhibitor can also be any substance that neutralizes or antagonizes the bioactivity of IL-3; it can also be a substance that prevents release of IL-3. Preferably, an IL-3 inhibitor is a substance blocking IL-3 or a substance that selectively reduces IL-3 release. In a preferred embodiment an IL-3 inhibitor is a substance that specifically blocks binding of IL-3 to the α-receptor subunit of the IL-3 receptor.

In a preferred embodiment an IL-3 inhibitor is selected from an antibody that specifically inhibits IL-3 or specifically blocks the binding of IL-3 to its receptor, or a derivative or a fragment thereof, or an agent that specifically inhibits IL-3 or specifically blocks the binding of IL-3 to its receptor or specifically blocks the production of IL-3, for example a ligand that binds to IL-3 or its receptor, a polypeptide or a peptide mimetic that binds to IL-3 or its receptor, an aptamer or Spiegelmer that binds to IL-3 or its receptor, DNA or RNA molecules that code for a peptide or polypeptide that has binding activity for IL-3 or its receptor or can modulate this binding, or soluble constructs that comprise parts of the IL-3 receptor and a fragment of IgG.

The term "antibody", whenever used in this application, shall comprise monoclonal antibodies and polyclonal antibodies as well as modified antibodies, like genetically engineered antibodies, chimeric antibodies, single chain antibodies, or humanized antibodies. Moreover, the term "antibody" when used in this application shall also include fragments, variants and multimers.

The term "fragment of an antibody" comprises any type of fragment that is well-known in the art, like inter alia $F_{ab}$-fragments or $F(ab')_2$ fragments, and has binding affinity for IL-3 or its receptor. The fragment can be derived from a polyclonal or monoclonal antibody. Methods for providing antibodies or antibody fragments are standard methods and are well known to the skilled person.

The term "ligand" as used herein relates to any compound having the ability to specifically interact such that IL-3 is blocked or inactivated. The interaction can be binding to IL-3 or the IL-3 receptor, whereby IL-3 is blocked or inactivated or can be binding to IL-3 activating substance.

The terms "peptide" or "polypeptide" respectively refer to a sequence of amino acids that can be obtained by chemical synthesis or by expression from a nucleic acid encoding the peptide or polypeptide or a combination thereof. The peptide or polypeptide can comprise naturally occurring amino acids, non-naturally occurring amino acids, modified amino acids or a combination thereof. Moreover, the peptide or polypeptide can have functional groups to introduce a function that is useful for binding to IL-3 or its receptor, for immobilizing a complex of the polypeptide or peptide with IL-3, or for modulation of the IL-3 signalling.

The term "nucleic acid encoding a peptide or polypeptide that inhibits or blocks or modulates IL-3" refers to a nucleic acid that can be selected from any biological or synthetic source or may be contained in nucleic acid libraries or databases. It includes DNA and RNA, and it includes nucleic acids that comprise modified nucleotides. The nucleic acid can be any type of nucleotide molecule like circular or linear and/or single-, double-stranded or partially double-stranded nucleic acid.

The term "aptamer" refers to DNA or RNA sequences that have binding activity for a specific molecule, in the present application to IL-3 or its receptor. Aptamers can be found by standard methods from random pools based on their ability to bind IL-3 or IL-3 receptor. Further information regarding aptamers are found in (36) and (37). Aptamers are strong binding oligonucleotides that bind to specific targets based on structural conformation. Aptamers can be identified from huge combinatorial nucleic acid libraries and can be amplified by PCR. The methods for screening libraries and amplifying the sequences are standard methods and well-known to the skilled person.

The terms "Spiegelmer" or "mirror image RNA" refer to nucleic acids that are similar to aptamers with regard to binding affinities and functionality but have a structure that prevents enzymatic degradation by using L-oligonucleotides instead of the natural D-oligonucleotides. Methods for screening and amplifying Spiegelmers are known in the art, for example from (38). In the present application Spiegelmers are used that bind IL-3 or IL-3 receptor.

The term "construct" as used in the present application refers to a molecule wherein specifically binding parts of the IL-3 receptor are connected with the FC part of an immunoglobulin. A preferred embodiment is a soluble construct comprising at least one α-receptor subunit and/or β-receptor subunit, or a derivative thereof having a similar binding capacity.

The term "prophylactic treatment" refers to treatment of a subject that has not developed symptoms of the disease but has a predisposition to develop the disease.

The term "early phases of exacerbation of rheumatoid arthritis" refers to that stage of the disease where the disease is in progression and the disease activity is still moderate or low and/or where the IL-3 level in joints and/or in plasma is detectable and/or increased compared to a standard where the standard is the average IL-3 level in the joints of healthy persons. Methods for the determination of the disease activity and methods for the determination of the IL-3 level in joints, tissue or any other sample are known in the art.

The term "maintenance therapy" refers to a treatment of rheumatoid arthritis during phases when the disease is not active or disease activity is low. The aim of maintenance therapy is to prevent disease exacerbation or disease progression.

The terms "increased" or "reduced" refer to a percentage or amount that is increased or reduced compared to the standard, i.e. a healthy person.

The term "disease activity" or the level of disease activity refers to the stage and severity of rheumatoid arthritis and can be evaluated using different disease scores. One disease score that is commonly used is the "disease activity score" (DAS-28). This score can be calculated based on the number of swollen joints, the number of painful joints, erythrocyte sedimentation rate and other factors. In the present application when it is referred to a disease activity score, this is a referral to DAS28. A DAS28 value of 0 to 3.2 indicates no disease or low disease activity; a DAS28 value between 3.2 and 5.1 corresponds to a moderate disease activity and a value beyond 5.1 corresponds to a high disease activity. The IL-3 inhibitor of the present invention is useful for disease phases with a DAS28 score of up to 5.1, particularly for DAS28 scores up to 3.2.

The invention is also explained with reference to the following Figures wherein

FIG. 1 shows IL-3 and basophils in collagen induced arthritis. Panel A, shows IL-3 production by splenocytes after restimulation with collagen. Panel B, shows measurement of synovial tissue cytokine levels. Panel C, indicates the influence of IL-3 on activation and survival of basophils. Panel D, shows the detection of basophils and mast cells in the synovial tissue of inflamed paws by flow cytometry.

Figure 2:
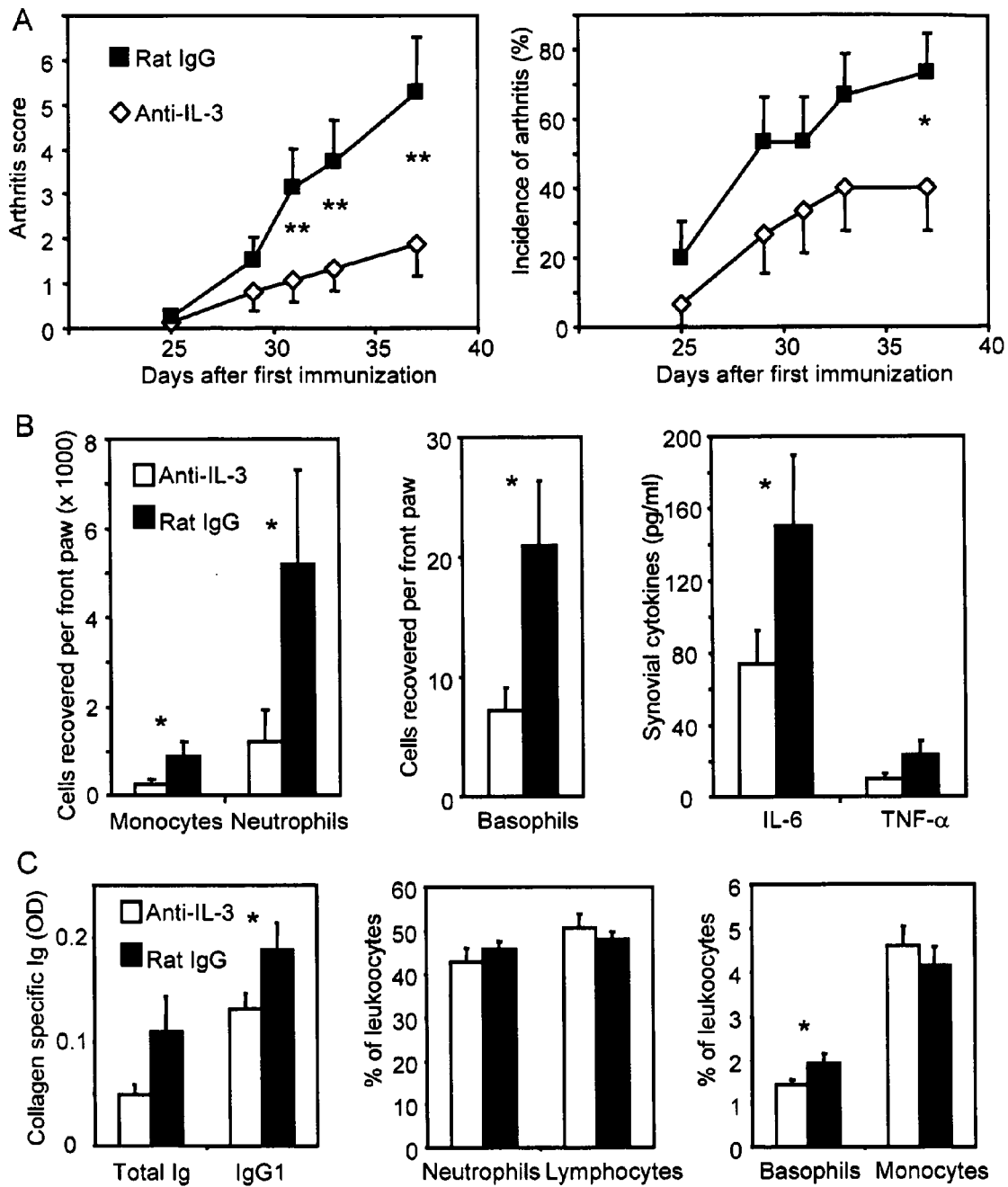

FIG. 2. shows the blockage of IL-3 during onset of arthritis, Panel A, shows Arthritis score and incidence in both groups. Panel B, provides the analysis of front paws at day 37 after the first immunization with collagen. Panel C, provides the analysis of plasma titers of collagen specific total Ig (plasma dilution 1:100,000) and collagen specific IgG1 (plasma dilution 1:5,000) (left panel) and peripheral blood leukocyte subsets (middle and right panel) at day 37 after the first immunization with collagen.

Figure 3:
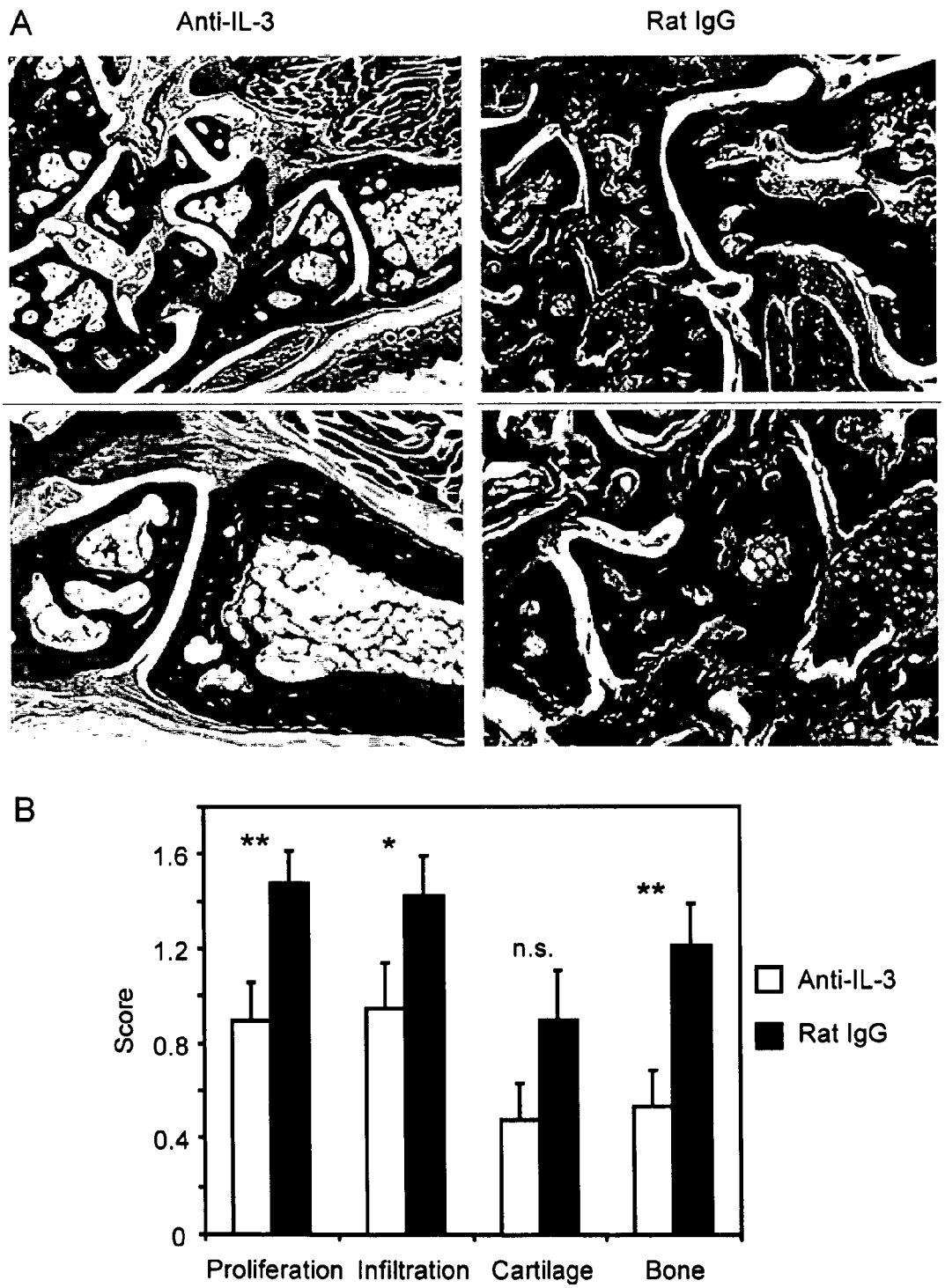

FIG. 3. shows the blockage of IL-3 during onset of arthritis. Panel. A, shows H&E-stained tissue sections of the tarsometatarsal joints of mice. Panel B, provides a summary of histological changes.

Figure 4:
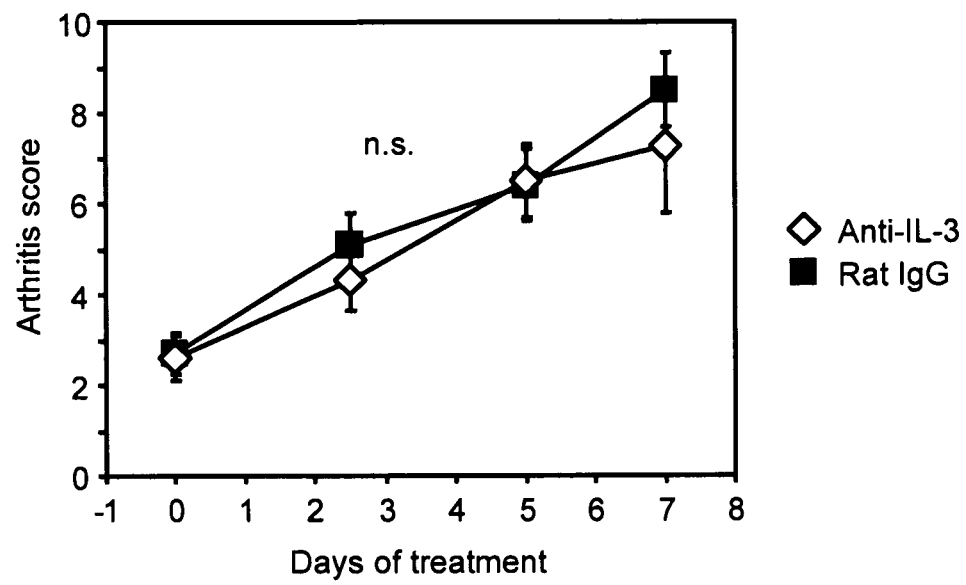

FIG. 4. shows the blockage of IL-3 after onset of arthritis.

Figure 5:
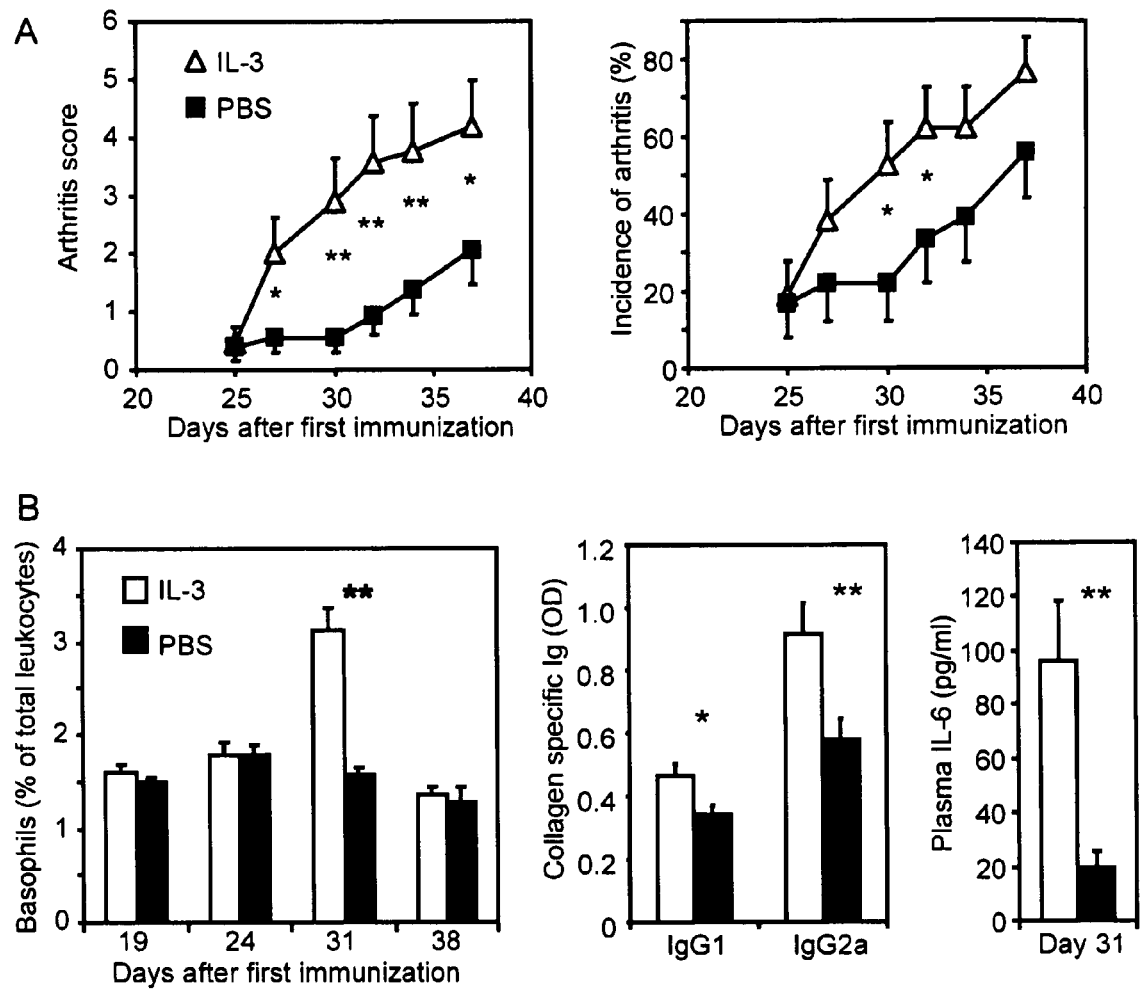

FIG. 5. shows that application of IL-3 exacerbates arthritis. Panel A, shows the data for arthritis score and incidence in both groups. Panel B, shows the frequency of basophils in the peripheral blood as determined by staining of cells with antibodies against IgE and CD45 and as percentage of total leukocytes (left panel) as well as plasma titers of collagen specific IgG1 and collagen specific IgG2a (middle panel) and plasma levels of IL-6 (right panel).

Figure 6:
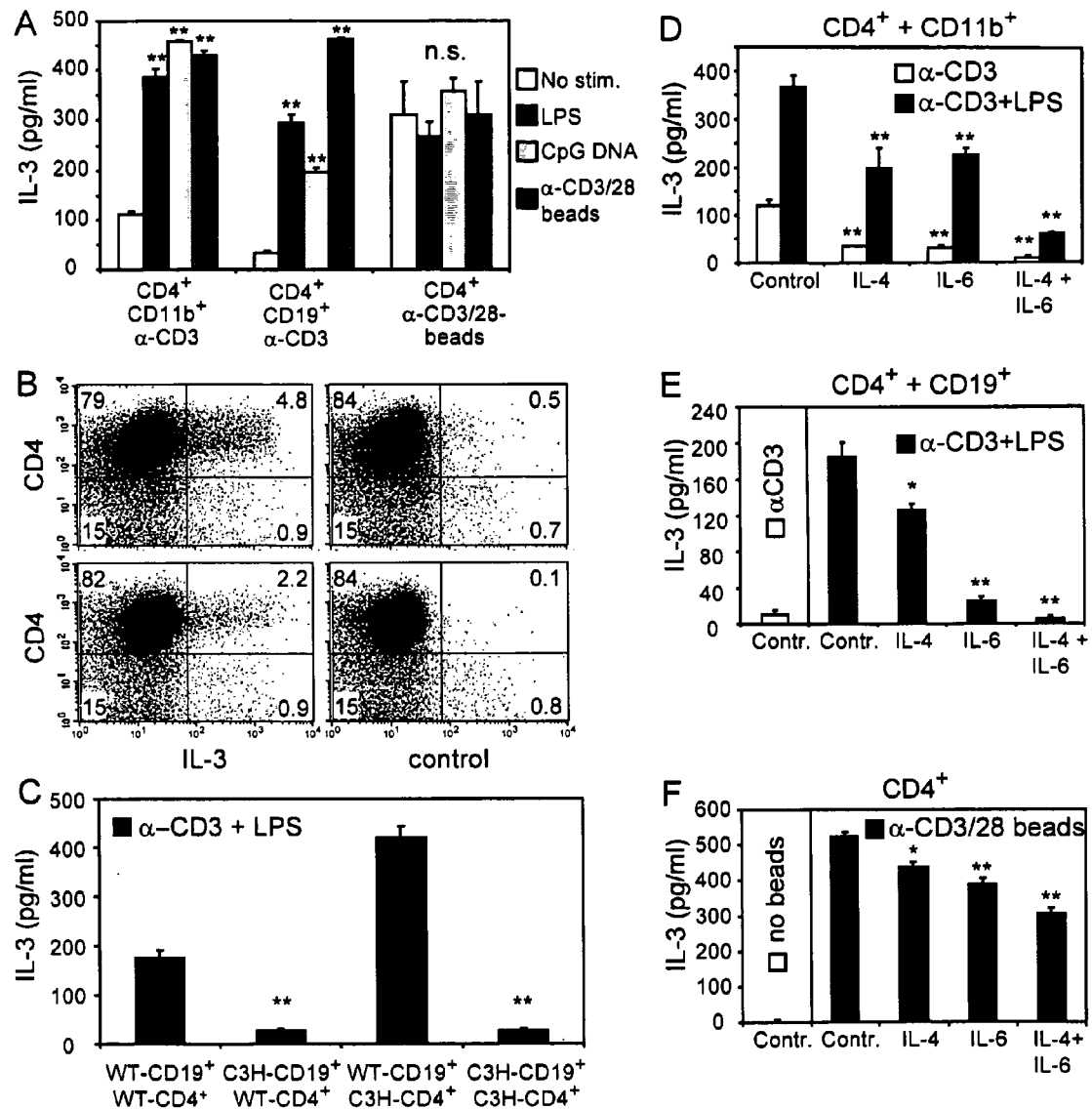

FIG. 6. shows the regulation of IL-3 secretion from $CD4^+$ T cells. Panel A, shows concentration of IL-3 for various cells. Panel B, shows the flowcytometric detection of intracellular IL-3 in $CD4^+$ T cells. Panel C, shows that LPS upregulates IL-3 expression of $CD4^+$ T cells by acting on $CD19^+$ B cells. Panel D-F, show that IL-4 and IL-6 suppress the release of IL-3 from activated $CD4^+$ T cells.

Figure 7:
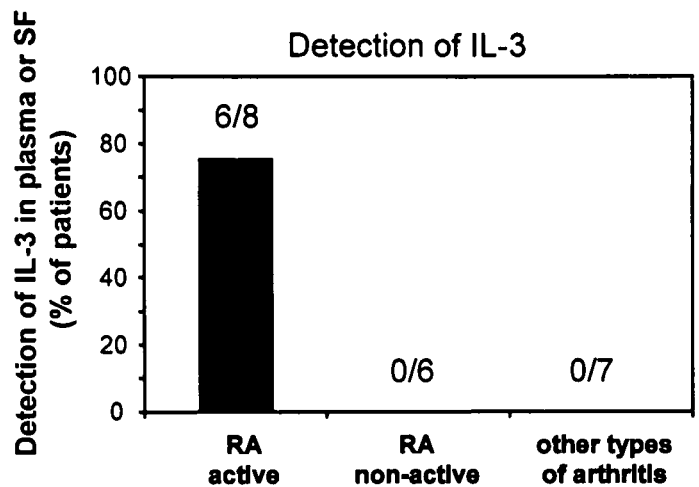

FIG. 7. shows the detection of IL-3 in patients with arthritis. It can be seen that IL-3 was detectable in 6 out of 8 patients with active RA but was not detectable in patients with non-active RA or other types of arthritis.

The inventors of the present invention surprisingly found that it is IL-3 that plays a role in the development of rheumatoid arthritis, particularly in the early phase of this disease. It seems that the availability of IL-3 is a disease-limiting factor. Moreover, they found that by inhibiting IL-3 the process of rheumatoid arthritis can be stopped and exacerbations or flares can be prevented or at least alleviated. Based on this finding the inventors developed a new strategy for fighting against the harmful disease RA. They were successful in providing a medicament that combines a selective treatment of RA with fewer side effects.

As one mechanism, the inventors found that basophils are an important cellular component involved in the rheumatic processes. It was observed that a marked aggravation of collagen-induced arthritis occurs by activation of basophils with antibodies against IgE. However, basophils are not only activated by cross-linkage of surface IgE, but also by other factors, particularly by IL-3. The basophils activated by IL-3 not only release IL-4 but also the pro-arthritogenic cytokine IL-6 which in turn has a detrimental effect. Moreover, the inventors found that basophils are an important cellular component of a memory immune response and that activation of basophils results in an exacerbation of rheumatoid arthritis. IL-3 as potent inducer and activator of basophils plays a significant role and it was found that IL-3 is present in synovial tissue during onset of arthritis. Surprisingly IL-3 is down-regulated when the inflammation has been developed and in the presence of high amounts of pro-inflammatory cytokines like IL-6. Therefore, if IL-3 is blocked during onset of arthritis, in an early stage of arthritis, or in an early phase of exacerbations this will result in reduced numbers of basophils in the peripheral blood and a profound improvement of clinical and histological signs of arthritis with reduced synovial leukocyte infiltration and reduced synovial levels of IL-6. It was found that using an agent that blocks IL-3 in the late phase of arthritis is mostly not effective.

The inventors concluded that by inhibiting IL-3 the further cascade could be stopped and, thus, the progressing of the inflammatory process that is characterizing for rheumatoid arthritis. Moreover, the inventors found that even very low concentrations of IL-3 not only induce a pronounced release of IL-6 from basophils but also prolong the survival of basophils in culture. As the basophils release pro-inflammatory cytokines, by inhibiting the activation of basophils and by inhibiting the longer survival of basophils the progress of RA can be stopped. Thus, an effect can be achieved by selective reduction of IL-3 release or by blocking of IL-3. It has been found that blockade of IL-3 is not associated with severe side-effects (for example (3)). In summary, the inventors showed that IL-3 increases the number of basophils in the peripheral blood, results in higher plasma levels of IL-6 and induces a marked exacerbation of arthritis.

Thus, the inventors concluded that rheumatoid arthritis can be treated by blocking IL-3 which causes that the progress of rheumatoid arthritis is stopped, basophils and other IL-3 responsive cells are no longer activated and the inflammation decreases.

Therefore, the present invention provides IL-3 inhibitors for use in the prophylactic treatment of rheumatoid arthritis, for the treatment of rheumatoid arthritis in an early stage, in early phases of exacerbation of rheumatoid arthritis and for use in maintenance therapy of rheumatoid arthritis.

In one embodiment of the present invention an IL-3 inhibitor, particularly an IL-3 inhibitor as defined above, is used for prophylactic treatment in a subject having a predisposition for developing rheumatoid arthritis to prevent that the disease erupts.

In a further embodiment of the present invention an IL-3 inhibitor is used for treatment of rheumatoid arthritis in an early stage as defined above. If rheumatoid arthritis in an early phase has been diagnosed in a subject, IL-3 inhibitor should be dosed as early as possible. Diagnosis of an early phase in patients can be achieved by using a disease activity score or by determining factors that are typical for rheumatoid arthritis. The presence of rheumatoid arthritis in an early phase can also be determined by determination of the IL-3 level in the inflicted joint. The determination of IL-3 can be done with analytical methods well-known to those of skill in the art. In order to find out if a subject suffers from an early stage of RA it is useful to determine the disease activity score as outlined above. If the value of the DAS28 is below 5.1, preferably below 3.2, this is an indication that a low to moderate activity of RA is present and that treatment with IL-3 inhibitor is highly indicated.

Another tool to determine the state of RA and for following the efficacy of the treatment with IL-3 inhibitor is measuring the amount of biomarkers like anti-CCP antibodies in the serum of a patient. Useful methods to measure CCP-antibodies are known in the art and are described in the literature. Methods for the determination of biomarkers like anti-CCP antibodies are disclosed for example in EP 1980855 and such methods are useful for the present invention.

In a further embodiment, the IL-3 inhibitor of the present invention is used for the treatment of an early phase of an exacerbation or flare or whenever the IL-3 level is increased in the progression of RA. It was found that also in a progressive stage of RA during flares the IL-3 level might rise. In these cases flares can be prevented or at least alleviated by dosing an IL-3 inhibitor. A useful tool for determining if a patient is in the early phase of an exacerbation or a flare-up is the DAS28. If the DAS28 value is starting to raise after a less painful period this is an indication for an exacerbation and, thus, for immediate treatment with the IL-3 inhibitor of the present invention.

It has been found that in an early stage or progressive/active stages of rheumatoid arthritis IL-3 is a disease limiting factor and that these stages are associated with a detectable and/or increased IL-3 level in the joint. In this regard an "increased IL-3 level" refers to an IL-3 level that is increased by more than 30% in relation to the normal IL-3 level.

It has been found that IL-3 is not or only in a very minute amount detectable in the synovial fluid or in the plasma of healthy patients or patients that have no active rheumatoid arthritis or other types of arthritis, whereas in those patients suffering from active rheumatoid arthritis an IL-3 level can be determined. Therefore, in a standard population where the IL-3 level is not detectable in persons not having active RA, an early phase of exacerbation of rheumatoid arthritis or an active state of rheumatoid arthritis is diagnosed in a patient where the IL-3 level in the plasma or in the synovial fluid is greater than 3 pg/ml of plasma or synovial fluid, preferably greater than 5 pg/ml, more preferably greater than 7.5 pg/ml and even more preferred at least 9.5 pg/ml of plasma or synovial fluid.

There are various ways to inhibit IL-3 that are all useful for treatment of RA. It is essential that IL-3 bioactivity is neutralized to avoid activation of basophils and other factors.

In one approach, the inhibition of IL-3 can be achieved by antibodies binding to IL-3 or to its receptor or to both such that the binding site of IL-3 or its receptor is blocked, for example sterically hindered. In another approach the inhibition can be achieved by a substance that has a higher affinity to IL-3 than the IL-3 receptor and therefore can block IL-3 or displace IL-3 from the receptor. The affinity of a substance compared to the affinity of IL-3 for its receptor can be determined by methods well-known to the skilled person, for example ligand binding assay.

If an antibody is used as IL-3 inhibitor, this can be any type of antibody, that is monoclonal as well as polyclonal antibodies or fragments thereof or DNA encoding them can be used. Thus, the term "antibody" or "antibodies" is used in a broad sense and includes both polyclonal and monoclonal antibodies and also includes fragments and multimers of immunoglobulin molecules, such as bi-specific and tri-specific antibodies, fusion proteins containing an antibody or antibody fragment which are produced using standard molecular biology techniques, single chain antibodies, and human or humanized versions of immunoglobulin molecules or fragments thereof. Any antibody or fragment thereof that specifically binds to IL-3 or the IL-3 receptor in a manner sufficient to block the binding of IL-3 to its receptor can be used for the present invention.

The antibody can bind to any part of IL-3 or the IL-3 receptor as long as the binding of IL-3 to its receptor is hindered. The antibody can bind to the α-receptor subunit or can block signal transduction by binding to the β-receptor subunit. As the inhibition shall be as specific as possible, preferably the anti-IL-3 antibody should bind to or block the α-receptor subunit. It is essential, that the anti-IL-3 antibody does not or only to a very low extent bind with other cytokines. An antibody that "selectively" binds to IL-3 is an antibody having a low cross reactivity with other cytokines, i.e. IL-5. Blocking anti-IL-3 antibodies are commercially available and are described in the literature, for example in J. Immunol. 1988, 140 (1:131-137) and in 32 to 35 below.

Antibodies useful for the present invention can be purchased from commercial sources. They can also be generated using methods well-known to the person skilled in the art. The skilled person knows which parts of IL-3 or the IL-3 receptor or complete IL-3 or cells expressing complete IL-3 receptors or parts thereof are useful as antigen to generate antibodies useful in the present invention. A polypeptide to be used for generating an antibody useful for the present invention may be partially or fully purified from a natural source or may have been synthesized using recombinant DNA techniques or peptide synthesis techniques that are well-known in the art. For example, a DNA encoding IL-3 or the IL-3 receptor or fragments thereof can be expressed in prokaryotic cells or eukaryotic cells, after which the recombinant protein can be purified and used to elicit an immune response in an animal to produce monoclonal or polyclonal antibodies. The skilled person knows how to choose the most suited part of a polypeptide to elicit an immune response in animals or to screen a phage library containing antibody fragments. If necessary, adjuvants can be used for producing antibodies as is well-known in the art. In one example, a peptide of at least twelve amino acids or more comprising the epitope and a peptide antibody package from a commercial source can be used. Moreover, two or more types of monoclonal antibodies or two or more charges of polyclonal antibodies can be produced and used in any combination, i.e. different types of monoclonal antibodies can be combined or different charges of polyclonal antibodies or monoclonal antibodies and polyclonal antibodies can be combined to obtain a preparation with the optimal specificity and affinity required for the inhibition of IL-3.

Testing antibodies for their activity and affinity are well-known in the art. Methods that are applicable are for example ELISA and immunocytochemistry, ligand binding assays, IL-3 dependent cell growth, cell activation and flow cytometry. Guidance can be found in textbooks like Harlow and Lane, Antibodies: A Laboratory Manual, Cold Spring Harbor Laboratory Press, Cold Spring Harbor, N.Y., 1988.

Monoclonal antibodies are obtained from a substantially homogeneous population of antibodies or antibody fragments, i.e. the individual antibodies within the population are identical in their specificity and affinity. Monoclonal antibodies include chimeric antibodies in which a portion of the heavy and/or light chain is identical with or homologous to corresponding sequences in antibodies derived from a particular species or belonging to a particular antibody class or subclass while the remainder of the chain is identical with or homologous to corresponding sequences in antibodies derived from another species or belonging to another antibody class or subclass, as well as fragments of such antibodies, as long as they exhibit the desired inhibitory activity.

Monoclonal antibodies useful for the present invention can be prepared using the well-known hybridoma technique as described by Köhler and Milstein, Nature, 256:495 (1975). To produce a hybridoma a mouse or other appropriate host animal is immunized with complete or an antigenic part of IL-3 or IL-3 receptor or fragments thereof to elicit lymphocytes that produce or are capable to produce antibodies that specifically bind to IL-3 or IL-3-receptor. Adjuvants that enhance the immune response can be used as is well-known in the art. Suitable lymphocytes are screened and immortalised by fusion with myeloma cells to obtain hybridomas.

The monoclonal antibodies can also be created by recombinant DNA methods that are well-known in the art. DNA encoding the monoclonal antibodies can be readily isolated and sequenced using conventional procedures. Libraries of antibodies or active antibody fragments can also be generated and screened using phage display techniques as is well-known in the art. Recombinant antibodies, antibody fragments, and fusions and polymers thereof can be expressed in vitro or in prokaryotic cells, such as bacteria, or eukaryotic cells, such as yeast, insects or mammalian cells, and further purified using well-known methods.

In vitro methods for preparing monovalent antibodies can also be used. Methods to produce fragments of antibodies are also well-known in the art. Thus, Fab fragments can be produced using papain, whereas $(Fab')_2$ fragments can be produced using pepsin.

Specifically binding anti-human IL-3 antibodies are commercially available, for example from R&D System Clones 4806 and 4815 (Catalog No. MAB203 and No. MAB603), and from BDBiosciences Clones BVD3-1F9 and BVD8-3G11 (Catalog No. 554674 Biotin Rat Anti-Human IL-3 0.5 mg; No. 554671 Purified NA/LE Mouse Anti-Human IL-3 0.5 mg) or have been published (F14-570, F14-746, J. Immunol. 1991, 146:893-898). In a preferred embodiment one of these antibodies or a fragment thereof is used as reference for specificity and affinity for IL-3; preferably antibodies are used that are binding to IL-3 at least with a specificity and affinity as one of these commercially available ones. Other anti-IL-3 antibodies can be used as well. The affinity of an antibody in comparison to a known antibody can be determined according to well-known methods known in the art, for example by competitive ELISA.

Tests to determine if one antibody has a similar neutralising activity or a similar epitope specificity as another antibody are routine for the skilled person and assays useful therefore are also known. Moreover, with the provision of a specifically binding antibody identification of the epitope that the monoclonal antibody recognizes can be performed as follows. First, various partial structures of the molecule that the monoclonal antibody recognizes are prepared. The partial structures are prepared by the method wherein various partial peptides of the molecule are synthetically prepared by known oligopeptide synthesis technique, or the method wherein DNA encoding the desired partial polypeptide is incorporated in a suitable expression plasmid, and is expressed in a suitable host, such as E. coli, to produce the peptides. Generally, both methods are frequently used in combination for the above object. For example, a series of polypeptides having appropriately reduced lengths, working from the C- or N-terminus of the antigen protein, can be prepared by established genetic engineering techniques. By establishing which fragments react with the antibody, an approximate idea of the epitope site is obtained. The epitope is more closely identified by synthesizing a variety of smaller oligopeptides corresponding thereto or mutants of the peptide using established oligopeptide synthesis techniques to determine a binding property of the peptides to the anti-IL-3 monoclonal antibody which is a basis for preparation of further antibodies useful for the present invention and a competitive inhibition of binding of the peptide to an antigen with the monoclonal antibody. Commercially available kits may be conveniently used to obtain a large variety of oligopeptides.

The term "antibody" can also refer to a human antibody and/or a humanized antibody. Non-human antibodies can give rise to undesirable immune responses when administered to humans and, therefore, should be humanized with methods well-known in the art.

In a preferred embodiment humanized antibodies are used according to the present invention. Antibody humanization techniques generally involve the use of recombinant DNA technology to manipulate the DNA sequence encoding one or more polypeptide chains of an antibody molecule. Accordingly a humanized form of a non-human antibody or a fragment thereof is a chimeric antibody or antibody chain or a fragment, such as an Fv, Fab, Fab' or other antigen-binding portion of an antibody which contains a portion of an antigen binding site from a non-human antibody integrated into the framework of a human antibody. In a preferred embodiment an antibody produced by one of the clones 4806, 4815, BVD3.1F9, BVD8-3G11, F14-570 or F14-746 is used in a humanised form.

To generate a humanized antibody residues from one or more complementary determining regions (CDRs) of a recipient antibody molecule are replaced by residues from one or more CDRs of a donor antibody molecule that is known to have the desired IL-3 or IL-3 receptor binding characteristics, for example an antibody produced by one of the clones 4806, 4815, BVD3.1F9, BVD8-3G11, F14-570, F14-746 mentioned above. Sometimes Fv framework residues of the human antibody can be replaced by corresponding non-human residues. Humanized antibodies can also contain other residues to introduce desired properties. Thus, for the present invention humanized antibodies are used that are human antibodies in which some CDR residues and possibly some framework residues are substituted by residues from analogous sites in an antibody produced by one of the clones 4806, 4815, BVD3.1F9, BVD8-3G11, F14-570, F14-746. Methods for humanizing non-human antibodies are well-known in the art. For example, humanized antibodies can be generated by substituting rodent CDRs or CDR sequences for the corresponding sequences of a human antibody.

Moreover, human antibodies can be prepared using techniques for human monoclonal antibody production as described in the art. For example, human antibodies can be produced using phage display libraries.

Human antibodies can also be obtained from transgenic animals. For example, transgenic, mutant mice that are capable of producing a full repertoire of human antibodies in response to immunization have been described in the art. Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity can be selected using well-known methods, like immunohistochemistry, ELISA, or Western Blot or flow cytometry.

Antibodies or antibody fragments can include insertions, deletions, substitutions, or other selected modifications of particular regions or specific amino acid residues to achieve specific properties. Moreover, antibodies or antibody fragments can be attached to other sequences or to specific groups to provide specific properties. For example modifications can be made to remove or add amino acids capable of disulfide bonding, to increase bio-longevity, to alter secretory characteristics, etc. All these modifications can be done provided that the antigen specificity and affinity is not significantly changed. Functional or active regions of the antibody or antibody fragment can be identified and/or improved by mutagenesis of a specific region of the protein, followed by expression and testing of the expressed polypeptide as is well-known to the skilled person. For example, amino acid sequence variants of antibodies or antibody fragments can be generated and those that display equivalent or improved affinity for IL-3 or the IL-3 receptor can be identified using standard techniques. Site-specific mutagenesis or random mutagenesis of the nucleic acid encoding the antibody or antibody fragment is also applicable and well-known to the skilled person. Both naturally occurring and non-naturally occurring amino acids may be used to generate amino acid sequence variants of the antibodies and antibody fragments.

All these types of antibodies and antibody fragments are useful for the present invention.

To select an antibody that is useful in the present invention its ability to neutralize the biological activity of IL-3 can be used. Antibodies that bind to human IL-3 or human IL-3 receptor in recombinant as well as natural form can be captured by using human IL-3 or human IL-3 receptor immobilized as well-known in the art.

Tests for the determination of IL-3 are commercially available, for example ELISA kits from BDBiosciences. (See also 32 to 34.)

The concentration of antibody that is required to neutralize IL-3 activity in a subject is dependent from cytokine concentration, cell type, growth conditions and type of activity. To provide a guideline, the neutralization dose of an antibody can be determined under a specific set of conditions. The neutralization dose ($ND_{50}$), for an antibody is defined as that concentration of antibody required to yield one half maximal inhibition of IL-3 activity or IL-3 receptor on a responsive cell line, when IL-3 is present at a concentration just high enough to elicit a maximum response. A typical concentration is in the range of 0.001 to 1 µg/mL using a TF-1 cell line proliferation assay. This assay is described by Kitamura T. et al., 1989, J. Cell Physiol. 140 (2):323-334. In this assay human IL-3 stimulates the $^3$H-thymidine incorporation by human TF-1 cells in a dose dependent manner. The $ED_{50}$ for this effect is typically 0.1 to 0.4 ng/mL. To measure the ability of an antibody to neutralize the bioactivity of IL-3 on human TF-1 cells, IL-3 can be incubated with various concentrations of the antibody for one hour at 37° C. in a 96 well plate. Following this pre-incubation period, TF-1 cells are added. The assay mixture in a total volume of 100 µl containing antibody in various concentrations between 0.001 to 10 µg/mL IL-3 at 1.25 ng/mL and cells at $1 \times 10^5$ cells/mL are incubated at 37° C. for 48 hours in a humidified $CO_2$ incubator. $^3$H-thymidine is added during the final four hours of incubation. The cells are subsequently harvested onto glass fibre filters and the $^3$H-thymidine incorporated into DNA is determined. Under these conditions the $ND_{50}$ of the antibody can be determined.

Thus, when using anti-human IL-3 antibodies or anti-human IL-3 receptor antibodies this test can be performed to find the optimal concentration of the antibody to neutralize IL-3.

The dosage of the antibody can be selected using such a neutralization test. When using IL-3 inhibitors according to the present invention, the $ID_{50}$ can be determined at the beginning of the therapy and in useful periods during a longer lasting therapy.

In further embodiments an agent that specifically inhibits IL-3 or specifically blocks the binding of IL-3 to its receptor or specifically blocks the production of IL-3 can be used. Examples are a ligand that binds to IL-3 or its receptor, a polypeptide or a peptide mimetic that binds to IL-3 or its receptor, an aptamer or Spiegelmer that binds to IL-3 or its receptor, DNA or RNA molecules that code for a peptide or polypeptide that has binding activity for IL-3 or its receptor or can modulate this binding, or soluble constructs that comprise parts of the IL-3 receptor and a fragment of IgG.

In one embodiment the ligand is a peptide or polypeptide, or a nucleic acid encoding a peptide or polypeptide that inhibits or blocks or modulates IL-3.

Another useful group of IL-3 inhibitors comprise aptamers and Spiegelmers as defined above. Aptamers and Spiegelmers that are particularly useful as IL-3 inhibitors are those that have binding activity for IL-3 or its receptor. Those aptamers and Spiegelmers can be found by standard methods from random pools based on their ability to bind IL-3 or IL-3 receptor. Preferably aptamers or Spiegelmers are used that bind to IL-3 or its receptor with Kds (equilibrium constant) in the range of 1 pM to 1 nM, similar to antibodies.

In another preferred embodiment of the present invention constructs are used comprising specifically binding parts of the IL-3 receptor conjugated to the FC part of an immunoglobulin. A preferred embodiment of such a construct is soluble and comprises at least one α-receptor subunit and/or β-receptor subunit, or a derivative thereof having a similar binding capacity.

In another approach soluble IL-3 receptor or fragments thereof are used to interfere with the binding of IL-3 to its receptor by occupying the binding sites of IL-3 and, thus, hindering that IL-3 can bind and activate.

In a further approach the production of IL-3 can be inhibited or decreased. Thus, any substance that hinders IL-3 production for example by monocytes or stimulated B-cells can be used for the present invention.

Moreover, it was found that the combination of IL-6 and IL-4 had a synergistic effect on the release of IL-3 and resulted in a very pronounced blockage of IL-3 production. This is shown in FIG. 6d, e. A combination of IL-6 and IL-4 can also reduce IL-3 secretion from CD4$^+$ T cells. Therefore, a further embodiment of the present invention is the provision of a factor such as IL-4 for inhibiting IL-3 production and thereby treating RA.

It has been found that as long as IL-3 is increased, rheumatoid arthritis is still progressing and the progression of rheumatoid arthritis can be inhibited or reduced by the use of the present invention, i.e. by using an IL-3 inhibitor for preparing a medicament for treating rheumatoid arthritis.

It was found that when using IL-3 inhibitor in an amount that decreases the IL-3 level or brings it to normal, the progression of RA can be delayed or even stopped, the cartilage destruction can be avoided or at least reduced, cell infiltration of synovial tissue can be reduced, and the production of basophils and release of IL-6 from basophils can be decreased.

In another approach, IL-3 can be depleted by using an IL-3 binding substance in immobilized form, particularly IL-3 antibodies. In that case one or more types of IL-3 binding molecules are bound to a solid phase using a group for immobilization. The solid phase can be for example a carrier, support, matrix, or beads. Groups for immobilization on a solid phase that can be used according to the present invention are well-known to the skilled person and those that are usually used to immobilize compounds can be used here, too.

As outlined above, any IL-3 inhibitor or in other words any substance that inhibits or blocks IL-3 or the binding of IL-3 to its receptor can be used for the treatment. The IL-3 inhibitor provides for treatment of rheumatoid arthritis in an early stage, particularly in patients where an increased level of IL-3 has been determined. Moreover, the IL-3 inhibitor can be used for prophylactic treatment to prevent that a subject that is predisposed for RA develops RA. In another embodiment the IL-3-inhibitor can be used for maintenance therapy for a subject that has developed RA but has no or a low disease activity to prevent the RA becomes severe. The IL-3 inhibitor neutralizes the bioactivity of IL-3 and thereby prevents or delays the progression of rheumatoid arthritis. Moreover it prevents or avoids cartilage destruction, cell infiltration of synovial tissue, and decreases the number of basophils.

An efficient dose for treatment can be determined by the physician as generally known in the art. An efficient dose of the inhibitor is an amount that alleviates the symptoms of RA or prevents an exacerbation of the disease. The progression of the disease can be followed by monitoring the IL-3 level and/or the disease score (e.g. DAS28) regularly. If the score is maintained or decreases by more than 0.6 the treatment is deemed to be efficient. Another indication for a successful therapy is a decreased or IL-3 level or no detection of IL-3 in plasma and/or synovial fluid. The dosage used for treatment is normally that dose that has the most favourable therapeutical index, that is has the highest effect with the lowest dose and the lowest side effects. This dosage can be determined using dose-response-curves as is well-known to the person of skill in the art.

If an IL-3 antibody is used the dosage depends from the activity and the half-life of the antibody. For antibodies having a half-life of about one to two weeks, the dosage is preferably in a range of 1 to 1000 mg, more preferable 10 to 100 mg per application. The antibody is applied once every day to once a month, preferably once every week or every other week, depending on the half life of the antibody in patients.

The optimal dosage is determined by a physician and adapted based on the course of the disease, preferably by using regular diagnosis of parameters like DAS28 values or other parameters.

In an alternative embodiment the dosage used for treatment can be determined by regularly monitoring the release of IL-3, the level of interleukin 6 (IL-6) and/or interleukin-4 (IL-4), that is cytokines that are released in response to IL-3.

Generally, a useful dosage of an IL-3 inhibitor is a dosage in the range from 0.01; 0.02; 0.03; 0.05; 0.07; 1.0; 1.5; 2.0; 2.5; or 30 mg of IL-3 inhibitor per kg weight of the subject per week up to 1.0; 1.5; 2.0; 2.5; 3.0; 4.0; 5.0; 7.0; 10; 12; 14; 17; or 20 g IL-3 inhibitor per kg weight of the subject per week.

The present invention moreover provides a pharmaceutical composition for the treatment of RA, particularly in an early stage comprising an IL-3 inhibitor and pharmaceutically acceptable carrier.

The carrier can be any additive, excipent or vehicle that is useful to prepare a pharmaceutical composition.

The IL-3 inhibitor of the present invention can be used for the treatment of rheumatoid arthritis in mammals, i.e. warm-blooded vertebrate animals, for example mammals of human, equine, porcine, bovine, murine, canine or feline species. Particularly the IL-3 inhibitor of the present invention is for use for human beings.

For the treatment of RA the IL-3 inhibitor can be used in any pharmaceutically acceptable form, such as in liquid or solid form. Preferably, the inhibitor is formulated as liquid that can be administered parenterally, particularly by intravenous, subcutaneous, intramuscular, intraarthicular injection. In a preferred embodiment the IL-3 inhibitor is provided for use for systemic or local administration. In one embodiment an agent that inhibits the binding of IL-3 to its receptor can be provided for use to be administered directly to the afflicted joint(s).

The dosage regimen depends from the severity of the disease, the age and weight of the subject to be treated, the inhibitor used, particularly its half-life under physiological conditions, and other well-known factors. A well suited regimen is an administration by i.v. or s.c. injection at least once per month, more preferably once within 3 to 15 days and, if necessary, more often.

Moreover, to further improve the treatment and increase efficiency, in a preferred embodiment, concomitantly with the use of IL-3 antibodies substances that modulate costimulatory cells can be used.

Furthermore, the inhibitor of the present invention can be used additionally to a classical RA treatment, for example in combination with NSAIDs and/or DMARDs (including biologicals).

Therefore, a further embodiment of the present invention is a composition comprising an IL-3 inhibitor in combination with an agent effective for treatment of RA selected from NSAIDs and DMARDs (including biologicals).

Thus, according to the present invention a useful tool for diagnosis and a useful treatment is provided. In a case, where rheumatoid arthritis has been diagnosed, and an increased IL-3 level has been determined, the use of an IL-3 inhibitor according to the present invention is highly indicated.

The following Figures are only illustrative to the present invention and shall describe particular embodiments of the present invention in further detail. However, these Figures are not intended to limit the subject matter of the present invention thereto.

FIG. 1. IL-3 and Basophils in Collagen Induced Arthritis.

A, IL-3 production by splenocytes after restimulation with collagen. On day 31 after the first immunization with collagen total splenocytes or splenocytes depleted of specific leukocyte subsets as indicated on the x-axis were incubated for 3 days with collagen type II. Collagen specific IL-3 production was determined by subtracting the IL-3 release in the absence of collagen. B, Measurement of synovial tissue cytokine levels. On day 36 after induction of arthritis hind paws of mice were scored and stratified in two groups with one having a clinical arthritis of 0-2 (n=14) and the other having a score of 3-4 (n=12). Synovial tissue of each paw was prepared in 1 ml PBS and cytokine levels were measured by ELISA. Highly inflamed paws contained significantly higher levels of TNF-α, IL-6 and IL-1β, but lower levels of IL-3. Synovial tissue levels of IL-17, GM-CSF and IFN-γ (did not correlate with the degree of inflammation. C, Influence of IL-3 on activation and survival of basophils. Basophils were enriched from the bone marrow of mice and cultured in triplicates for up to 4 days in the presence of various concentrations of IL-3, as indicated. In the absence of IL-3 no release of IL-6 and IL-4 was detectable and a rapid cell death of basophils occurred. Cytokine release and survival of basophils was markedly increased by addition of low amounts of IL-3. D, Detection of basophils and mast cells in the synovial tissue of inflamed paws by flow cytometry. Single cell suspensions were prepared from synovial tissue of inflamed paws by digestion with collagenase. Cells were analyzed for expression of CD45, c-kit and IgE and the frequency of basophils (IgE⁺, c-kit-) and mast cells (IgE⁺, c-kit⁺) is given as percentage of total CD45⁺ infiltrating leukocytes.

FIG. 2. Blockade of IL-3 During Onset of Arthritis.

Mice were treated with daily injections of 35 μg α-IL-3 (n=15) or rat IgG (n=15) from day 21-36 after the first immunization with collagen. A, Arthritis score and incidence were determined in both groups. B, Analysis of front paws at day 37 after the first immunization with collagen. The cells recovered from the synovial tissue were stained with antibodies against IgE, CD11b, CD45 and GR-1 to identify monocytes (CD11b⁺, GR-1$^{-/low}$), neutrophils (CD11b⁺, GR-1⁺) and basophils (IgE⁺, GR-1⁻). The absolute number of cells recovered per front paw is shown in the left and middle panels. The amount of IL-6 and TNF-α present in the synovial tissue was quantified by ELISA (right panel). C, Analysis of plasma titers of collagen specific total Ig (plasma dilution 1:100,000) and collagen specific IgG1 (plasma dilution 1:5,000) (left panel) and peripheral blood leukocyte subsets (middle and right panel) at day 37 after the first immunization with collagen. Peripheral blood cells were stained and identified as described in FIG. 2b and leukocyte subsets are given as percentage of total leukocytes.

FIG. 3. Blockade of IL-3 During Onset of Arthritis.

Mice (n=15 per group) were treated as described in FIG. 2 and the histological chances of the lower tarsometatarsal joints were determined on day 37 after the first immunization with collagen. A, H&E-stained tissue sections of the tarsometatarsal joints of mice. Low grade synovial hyperplasia without cartilage or bone destruction in an anti-IL-3 treated mouse (left). Heavy bone and mild cartilage destruction with pronounced synovial hyperplasia in a control mouse (right). B, Summary of histological changes. Synovial hyperplasia (Proliferation), leukocyte infiltration (Infiltration), cartilage erosion (Cartilage) and bone destruction (Bone) were evaluated on a scale from 0-2.

FIG. 4. Blockade of IL-3 after Onset of Arthritis.

After induction of arthritis mice were evaluated daily for appearance of arthritis. When the arthritis score was at least 2, each mouse was randomly assigned for daily i.p. treatment with anti-IL-3 (n=10) or rat IgG (n=10). The day of the first application of anti-IL-3 or rat IgG was assigned day 0 and the treatment was continued until day 6. Blockade of IL-3 did not reduce the progression of already established arthritis.

FIG. 5. Application of IL-3 Exacerbates Arthritis.

Mice were treated by twice daily i.p. injections of 100 ng IL-3 (n=21) or PBS (n=18) from day 20 to day 30 after the first immunization with collagen. A, Arthritis score and incidence were determined in both groups. B, The frequency of basophils in the peripheral blood was determined by staining of cells with antibodies against IgE and CD45 and is given as percentage of total leukocytes (left panel). Plasma titers of collagen specific IgG1 (plasma dilution 1:1,000) and collagen specific IgG2a (plasma dilution 1:2,000) (middle panel) and plasma levels of IL-6 (right panel) were determined by ELISA at day 31 after the first immunization with collagen FIG. 6. Regulation of IL-3 Secretion from CD4⁺ T Cells.

A, As indicated on the x-axis CD4⁺ T cells were cultured for 3 days with CD11b⁺ cells and α-CD3, with CD19⁺ B cells and α-CD3 or with α-CD3/28 beads. LPS (10 μg/ml), CpG DNA (1 μM) or α-CD3/28 beads (50,000 per well) were also added as indicated in the figure legend. The concentration of IL-3 was measured in the supernatant by ELISA. B, Flowcytometric detection of intracellular IL-3 in CD4⁺ T cells cultured for three days with CD11b⁺ cells, α-CD3 and LPS (upper panels) or with B cells, α-CD3 and LPS (lower panels). IL-3 is only detectable in CD4⁺ T cells. C, LPS upregulates IL-3 expression of CD4⁺ T cells by acting on CD19⁺ B cells. CD4⁺ T cells from wild-type mice (WT) or from TLR4-deficient C3H mice (C3H) were stimulated for 3 days with α-CD3 and LPS in the presence of B cells from wild-type mice or in the presence of B cells from C3H mice as indicated on the x-axis. The concentration of IL-3 was measured in the supernatants by ELISA. D-F, IL-4 and IL-6 suppress the release of IL-3 from activated CD4⁺ T cells. CD4⁺ T cells were cultured for 3 days with CD11b⁺ cells and α-CD3 or with CD11b⁺ cells, α-CD3 and LPS (panel D), or with CD19⁺ B cells and α-CD3 or with CD19⁺ B cells, α-CD3 and LPS (panel E), or without stimulation or with α-CD3/28 beads (panel F). IL-4, IL-6 or both were added at a concentration of 10 ng/ml each as indicated on the x-axis. The concentration of IL-3 was measured in the supernatants by ELISA.

FIG. 7. shows the detection of IL-3 in patients with arthritis. It can be seen that IL-3 was detectable in 6 out of 8 patients with active RA but was not detectable in patients with non-active RA or other types of arthritis.

Results.

IL-3 is produced in large quantities by collagen specific CD4+ T cells in the spleen and is present in the synovial tissue during onset of arthritis but is downregulated in paws with severe inflammation. Blockade of IL-3 during onset of arthritis results in a profound improvement of arthritis with reduction of synovial leukocytes, synovial cytokines, antibody titers against collagen and peripheral blood basophils. Blockade of IL-3 in the late phase of arthritis has no beneficial effect. Application of recombinant IL-3 during onset of arthritis induces a marked exacerbation of arthritis with increased peripheral blood basophils, increased plasma IL-6 and increased antibody titers against collagen. In addition, we investigated how expression of IL-3 is regulated in CD4⁺ T cells and show that IL-6 and IL-4 suppress the release of IL-3 by activated CD4⁺ T cells, whereas LPS and CpG-DNA upregulate IL-3 secretion from activated CD4⁺ T cells by acting on costimulatory cells.

Preferred embodiments of the invention are outlined in the following examples which should not be interpreted as restricting the scope or spirit of the invention.

EXAMPLE 1

Introduction

The role of IL-3 in arthritis was analyzed. Recently a marked aggravation of collagen induced arthritis by activation of basophils with antibodies against IgE was observed. Basophils cannot only be activated by crosslinkage of surface IgE but also by other factors, especially IL-3. Basophils not only release IL-4 but also the pro-arthritogenic cytokine IL-6 (see below). Even very low concentrations of IL-3 induce a pronounced release of IL-6 from murine basophils and prolong the survival of basophils in culture (see below). In the model of collagen induced arthritis in DBA/1 mice the expression of IL-3 in the paws at various stages of the disease was analyzed, the number of basophils and mast cells in the synovial tissue quantified and it was investigated how disease incidence and activity is influenced by blockade or administration of IL-3. In addition, the regulation of IL-3 release from T cells in vitro was studied to better understand the stage specific release of IL-3 in arthritis.

Materials and Methods

Induction of Collagen Induced Arthritis—Treatment of Mice

Arthritis was induced in male DBA/1 mice by a first intra-/subcutaneous injection of 100-200 μg bovine collagen type II (Sigma C1188) in complete Freund's adjuvant at the tail base on day 0 and restimulation of mice by intraperitoneal injection of 100-200 µg collagen type II without adjuvant on day 21. The clinical score of arthritis was evaluated in a blinded fashion as follows: 0, normal; 1, swelling in one joint; 2, swelling in more than one joint; 3, swelling of the entire paw; 4, deformity and/or ankylosis. For the experiment shown in FIGS. 2 and 3 animals were treated by daily i.p. injections of 35 µg of a blocking anti-IL-3 antibody (clone MP2-8F8, Biozol, Germany) or purified rat IgG (Sigma-Aldrich) from day 21-36. Mice were sacrificed on day 37. For the experiment shown in FIG. 4 daily i.p. treatment with 50 µg anti-IL-3 antibody or purified rat IgG was started when the arthritis score of an individual mouse was at least 2. Treatment was continued for seven days. For the experiment shown in FIG. 5 mice were treated from day 20-30 with twice daily i.p. injection of 100 ng IL-3 (Peprotec) or PBS. The clinical score of arthritis was evaluated as follows: 0, normal; 1, swelling in one joint; 2, swelling in more than one joint; 3, swelling of the entire paw; 4, deformity and/or ankylosis. Animal experiments were performed in accordance with the legal requirements of the Government of Bavaria (Az. 55.2-1-54-2531-109-05).

Preparation of Synovial Tissue—Quantification of Cytokines and Infiltrating Cells Paws were removed at the ankle joint, the skin was removed from the inflamed paws and the remaining tissue was carefully recovered with a scalpel in a volume of 500 µl/1000 µl PBS for front/hind paws. Without delay samples were centrifuged for 10 min at 400×g. The supernatant was immediately frozen and used for ELISA of cytokines. The synovial tissue was digested with collagenase I (Sigma) for 20 min at 37° C. to obtain a single cell suspension and used for FACS analysis.

Histological Analysis

Hind paws were fixed in 3.7% formalin for 24 h, decalcified with RDO rapid decalcifier (Medite GmbH, Germany) and embedded in paraffin. At least ten 5 µm thick sections of the tarsometatarsal joints were stained with HE and evaluated in a blinded fashion on a scale from 0 (normal) to 2 for all categories: synovial inflammation (1, focal inflammatory infiltrates; 2, inflammatory infiltrate dominating the cellular histology), synovial hyperplasia (1, continuous, at least three layer thick synovial lining in one joint; 2, in several joints), pannus formation and cartilage loss (1, cartilage partially covered by pannus, no cartilage loss; 2, with cartilage loss) and bone destruction (1, small areas of bone destruction; 2, widespread bone destruction).

Flow Cytometry, ELISA, Cytokines

The following antibodies were used for flow cytometry or magnetic cell separation: fluorescein isothiocyanate-anti-CD45 (LCA; 30-F11), allophycocyanin-anti-CD45 (LCA; 30-F11), fluorescein isothiocyanate-anti-CD11b (M1/70), phycoerythrin-anti-CD11 b (M1/70), Fc-block (2.4G2), phycoerythrin-anti-CD19 (1D3), allophycocyanin-anti-GR-1 (RB6-8C5), allophycocyanin-anti-CD4 (RM4-5), phycoerythrin-anti-c-kit(2B8), fluorescein isothiocyanate-anti-IgE (R35-72), phycoerythrin-anti-IL-3 (MP2-8F8), fluorescein isothiocyanate- and phycoerythrin-labelled isotype controls (all BD-Biosciences), allophycocyanin-anti-CD49b (DX5; Miltenyi). Unfixed cells were preincubated for 15 min on ice with Fc-block (5 µg/ml) and then with combinations of directly labeled antibodies for 45 min on ice. After 3 washing steps red blood cells were lysed with FACS-lysing solution (BD-Biosciences) and samples were analyzed on a FACS-Calibur (BD-Biosciences). For quantification of intracellular IL-3, cells were first stained with allophycocyanin-anti-CD4, and then treated with Fix-Perm and Perm-Wash solutions (BD Bioscience) according to manufacturer's instructions and stained with a PE-labelled antibody against IL-3.

IL-3, IL-4 and IL-6 were measured with commercially available ELISA kits from BDBiosciences. IL-1β, IFN-γ, TNF-α, GM-CSF and IL-17 were measured with ELISA kits from R&D-Systems (Quantikine). Antibodies against collagen were quantified by ELISA. Collagen (20 µg/ml) was coated overnight on ELISA-plates. Plasma samples were diluted in PBS/3% BSA as indicated in the figure legends. Immunoglobulins bound to collagen were detected with a HRP-labelled polyclonal rabbit-anti-mouse antibody (P260, DAKO), or HRP-labelled monoclonal antibodies specific for murine IgG1 (clone LO-MG1-2, Serotec) or for murine IgG2a (clone R19-15, BD-Pharmingen).

The murine cytokines IL-3, IL-4 and IL-6 were obtained from Peprotec.

Isolation and Culture of Cells

Splenocytes from mice with collagen induced arthritis were depleted of B cells and $CD4^+$ T cells with magnetic beads directed against CD19 and CD4 (Miltenyi). Basophils, monocytes or neutrophils were depleted by incubation of splenocytes with fluorochrome labelled antibodies against IgE, CD11b or GR-1 and subsequent incubation with magnetic beads directed against the fluorochrome. Total splenocytes or splenocytes depleted of a specific leukocyte subset were cultured in 96-well flat bottom plates (2 Mio cells/200 µl medium) for 3 days with or without bovine collagen type II (40 µg/ml). Cell culture supernatant was used for ELISA and collagen specific release of IL-3 was determined as follows: IL-3 release with collagen–IL-3 release without collagen.

$CD4^+$ T cells, B cells and monocytes were isolated from the splenocytes of C57BL/6 or TLR-4 deficient C3H mice (Charles River) using magnetic microbeads against CD4, CD19 and CD11b (Miltenyi), respectively. The purity of the isolated cells was routinely over 95%. Cells were cultured for 3 days in round-bottom 96 well plates in a total volume of 200 µl medium/well (RPMI-1640 with 10% FCS and 1% Pen/Strep). The number of cells per well was 50,000 for each cell type. Beads coated with antibodies against CD3 and CD28 (T cell expander beads, Dynal/Invitrogen) were used at a concentration of 50,000 beads/well. As indicated the following reagents were added: antibodies against CD3 (0.5 µg/ml, clone 2C11), LPS (10 µg/ml, Sigma), CpG-DNA (1 µM, PG1668=TCCATGACGTTCCTGATGCT, TIB-MolBiol), IL-4 (10 ng/ml), IL-6 (10 ng/ml). The concentration of IL-3 was determined by ELISA in the culture supernatant after 3 days. For intracellular staining of IL-3, $CD4^+$ T cells were activated for 3 days with α-CD3 and LPS in the presence of B cells or monocytes. PMA (10 ng/ml) and ionomycin (1 µg/ml) were added during the last 4 h of culture and brefeldin A (5 µg/ml) was added during the last 2.5 h of culture.

Basophils were enriched from the bone marrow of C57BL/6 mice with magnetic microbeads against DX-5 and LS-columns (Miltenyi). Basophils were identified by low expression of CD45 and high expression of DX-5 and constitute about 10% of the enriched cells. Basophils (1,100 cells/well) were cultured for various periods of time in round-bottom 96 well plates in a total volume of 200 µl medium/well (RPMI-1640 with 10% FCS and 1% Pen/Strep) with various concentrations of recombinant IL-3. The concentration of IL-4 and IL-6 was measured in the cell culture supernatant by ELISA. The number of live basophils per well was quantified for each time point by flow cytometry after staining of total cells with antibodies against CD45 and DX-5 in combination with propidium iodide (10 µg/ml) and counting beads (Coulter).

Statistics

Error bars indicate the standard error of the mean in all figures. Cell culture experiments were performed in triplicates. P values for significance were calculated with a one sided Students T-test and indicated with one asterisk ($p<0.05$) or two asterisks ($p<0.01$).

Results

IL-3 and Basophils in Collagen Induced Arthritis

We first wanted to know, if IL-3 is produced in the spleen and synovial tissue of mice with arthritis. At day 31 after the first immunization with collagen we restimulated total splenocytes or splenocytes depleted of specific leukocyte subsets with collagen and determined the collagen specific release of IL-3 by subtracting the release of IL-3 in the absence of collagen (FIG. 1a). Total splenocytes, or splenocytes depleted of $CD19^+$ cells (B cells), $IgE^+$ cells (basophils) or $GR-1^+$ cells (mainly neutrophils) produced large amounts of IL-3 after stimulation with collagen. In contrast, depletion of $CD4^+$ T cells or $CD11b^+$ cells (mainly monocytes) completely abrogated the collagen specific release of IL-3, indicating that IL-3 production requires both, the presence of $CD4^+$ T cells and $CD11b^+$ costimulatory cells (FIG. 1a). B cells are neither necessary nor sufficient to support IL-3 production by $CD4^+$ T cells. The increased release of IL-3 in the absence of B cells results from a higher number of T cells and monocytes in the assay, as the total number of leukocytes per well was kept constant and B cells constitute over 50% of the leukocytes in the spleen. Cytokine production in the synovial tissue of hind paws was measured at day 36 after the first immunization with collagen (FIG. 1b). For that purpose the paws were dissected at the ankle joint, the skin was removed and the soft tissue completely recovered in 1 ml PBS. After centrifugation for 10 min at 400×g cytokines were measured in the supernatant by ELISA. Paws were stratified in two groups according to the degree of clinical apparent arthritis with 14 paws having a score of 0-2 and 12 paws having a score of 3-4. As expected paws with a pronounced inflammation had high levels of IL-6 and IL-1β (683 and 619 pg/ml, respectively) while paws with no or low grade inflammation had several fold lower IL-6 and IL-1β levels (144 and 72 pg/ml, respectively). TNF-α was detectable only at very low levels, but was increased in paws with a score of 3-4. In contrast, IL-3 was readily detectable in paws with a score of 0-2 (66 pg/ml), but was highly significantly reduced in paws with severe inflammation (14 pg/ml). Local levels of IL-17, GM-CSF or IFN-γ did not correlate with the degree of paw inflammation (FIG. 1b).

IL-3 is known to induce and facilitate the histamine and IL-4 release from basophils. We show that IL-3 by itself also induces a high release of IL-6 from murine basophils and markedly prolongs the survival of isolated basophils in culture (FIG. 1c). Release of IL-6 is observed at very low IL-3 concentrations (half-maximal release at about 0.3 ng/ml of IL-3). IL-3 also induced a release of IL-4 from basophils, whereby the release of IL-3 was about 3-fold lower than the release of IL-6 (data not shown). In the absence of IL-3, only 6% of the basophils survived a 4 day culture in medium, while addition of IL-3 increased the survival of basophils to about 60% (FIG. 1c).

We analyzed by flow cytometry, if basophils and mast cells are present in the inflamed paws of mice with collagen induced arthritis. Synovial tissue from inflamed paws was digested with collagenase to obtain a single cell suspension. Cells were stained with antibodies against IgE, c-kit and CD45 to identify basophils ($IgE^+$, $c-kit^-$, $CD45^{low}$) and mast cells ($IgE^+$, $c-kit^+$, $CD45^+$). While basophils were unambiguously detectable in all inflamed paws at a frequency of about 0.4% of total infiltrating $CD45^+$ leukocytes, only very few mast cells were found in some inflamed paws with a 20-fold lower frequency than basophils (FIG. 1d). The majority of infiltrating cells were monocytes and neutrophils, which are also known to be responsive to IL-3.

Functional Analysis of IL-3 in Collagen Induced Arthritis

The presence of IL-3 in early forms of collagen induced arthritis and the presence of cells (e.g. basophils and monocytes) that are able to respond to IL-3 by releasing pro-arthritogenic cytokines like IL-6 or IL-1 suggest that IL-3 might be involved in the pathogenesis of arthritis.

We therefore investigated if blockade of IL-3 with a monoclonal antibody improves the incidence and severity of arthritis in mice injected with 200 µg collagen type II on day 0 and day 21. One group of mice (n=15) received daily i.p. injections of the anti-IL-3 antibody (35 µg/day) from day 21-36, while the control group was injected with rat IgG at the same dose and time intervals. Blockade of IL-3 during disease onset highly significantly reduced the severity of clinical apparent arthritis. At day 37 the mean arthritis score of the control group was 5.3, while the mean arthritis score of the treatment group was 1.9 (FIG. 2a). Also the incidence of arthritis was significantly reduced by about 50% at day 37 (FIG. 2a). At day 37 we used the front paws for analysis of cells infiltrating the synovial tissue and for measurement of IL-6 and TNF-α in the supernatant of the recovered synovial tissue (500 µl/paw). The hind paws were used for histological evaluation. The number of monocytes, the number of basophils and the total number of $CD11b^+$ cells (including monocytes and neutrophils) recovered per front paw was significantly reduced in mice treated with anti-IL-3. Also the level of IL-6 measured in the recovered synovial tissue was significantly reduced in mice treated with anti-IL-3 (FIG. 2b). Histological analysis of the hind paw showed that the degree of synovial proliferation and bone destruction was highly significantly reduced in anti-IL-3 treated mice. The degree of infiltrating cells was significantly less and there was a trend towards reduced cartilage destruction (p=0.06) in anti-IL-3 treated mice (FIG. 3). Plasma titers of antibodies (IgG1 and IgG2a) against collagen were reduced in anti-IL-3 treated mice on day 37 (FIG. 2c). FACS-analysis of the peripheral blood on day 37 showed a mild but significant reduction in the frequency of basophils without significant alterations in the frequencies of neutrophils and monocytes (FIG. 2c). These data show that IL-3 plays an important role for induction and early progression of collagen induced arthritis.

We next analyzed if blockade of IL-3 is able to reduce the progression of already established arthritis. Mice were immunized twice with 200 µg collagen type II and checked daily for development of arthritis. When the arthritis score of an individual mouse was at least 2, treatment (daily i.p. application of 50 µg antibody) was started either with the anti-IL-3 antibody (n=10, arthritis score of 2.6 before treatment) or control IgG (n=10, arthritis score of 2.7 before treatment). As shown in FIG. 4 blockade of IL-3 did not reduce the progression of already established arthritis. These data indicate that IL-3 is not involved in late progression of arthritis. These data correlate with the reduced expression of IL-3 in paws with severe inflammation (see FIG. 1).

We also investigated, if application of IL-3 during disease onset could increase the incidence and severity of arthritis. Mice were immunized with 100 µg collagen type II on day 0 and day 21. One group of mice (n=21) was treated from day 20-30 with twice daily i.p. injection of 100 ng IL-3, while the control group (n=18) was injected with the same volume of PBS. Injection of IL-3 during disease onset significantly increased the incidence and severity of collagen induced arthritis (FIG. 5). On day 31 (1 day after the last injection of IL-3), mice treated with IL-3 showed significantly increased plasma titers of antibodies against collagen, 2-fold increased numbers of peripheral blood basophils and almost 5-fold increased plasma levels of IL-6. Basophilia and increased IL-6 plasma levels were transient, as no significant differences between IL-3 and PBS treated mice were detectable on day 37 (7 days after the last injection of IL-3). These data suggest that availability of IL-3 limits disease onset and progression in DBA/1 mice immunized with collagen type II.

Regulation of IL-3 Production by CD4$^+$ T Cells

Activated CD4$^+$ T cells are considered as the main cellular source of IL-3. However, there is little information on how IL-3 secretion by T cells is regulated. We therefore investigated in vitro which factors up- or downregulate IL-3 production. Polyclonal activation of purified CD4$^+$ T cells with a soluble antibody against CD3 and B cells as accessory cells resulted in little production of IL-3. If CD11b$^+$ monocytes were used as accessory cells, IL-3 production by CD4$^+$ T cells activated with soluble α-CD3 was upregulated more than 3-fold (FIG. 6a). Addition of the TLR ligands LPS and CpG-DNA markedly enhanced IL-3 secretion by polyclonally activated CD4$^+$ T cells in the presence of accessory B cells or monocytes (FIG. 6a). Stimulation of CD4$^+$ T cells and accessory cells with LPS or CpG DNA in the absence of α-CD3 did not result in a detectable release of IL-3 (data not shown). Activation of CD4$^+$ T cells with a combination of antibodies against CD3 and CD28 immobilized on beads resulted in a very high release of IL-3 independent of the presence of accessory cells or stimulation with LPS or CpG DNA (FIG. 6a). To demonstrate that IL-3 is produced by CD4$^+$ T cells and not B cells or monocytes we measured intracellular levels of IL-3 by flow cytometry (FIG. 6b). CD4$^+$ T cells were cultured for 3 days with α-CD3 in the presence of LPS-stimulated B cells or LPS-stimulated monocytes. Intracellular staining for IL-3 was only detectable in CD4$^+$ T cells and not in CD4 negative B cells or monocytes. Using TLR-4 deficient mice (C3H mice) we analyzed in more detail how LPS enhances the release of IL-3 (FIG. 6c). If the accessory B cells were unable to respond to LPS, no enhanced release of IL-3 by CD4$^+$ T cells was detectable. If TLR-4 deficient CD4$^+$ T cells were used, IL-3 production was increased rather than reduced. These data indicate that LPS increases the release of IL-3 by CD4$^+$ T cells by stimulating accessory cells and that the level of costimulation provided to CD4$^+$ T cells critically influences the expression of IL-3.

Based on our finding that IL-3 levels are downregulated in paws with severe arthritis, we investigated if cytokines present at high concentrations in the inflamed joints are able to downmodulate IL-3 expression by activated CD4$^+$ T cells. For that purpose CD4$^+$ T cells were activated in the presence of various cytokines (IL-6, IL-4, IL-18, TNF-α, MIP-2). Addition of IL-β, TNF-α or MIP-2 had no effect on the release of IL-3 (data not shown). However, addition of IL-6 or IL-4 significantly reduced the IL-3 release by activated CD4$^+$ T cells independently of the costimulatory factors used for T cell activation (unstimulated monocytes, LPS stimulated B cells or monocytes and anti-CD3/28 coated beads) (FIG. 6d-f). The combination of IL-6 and IL-4 was synergistic and resulted in a very pronounced blockade of IL-3 production (FIG. 6d, e). IL-6 and IL-4 also reduced IL-3 secretion from CD4$^+$ T cells activated just with anti-CD3/28 coated beads, indicating, that IL-6 and IL-4 act on CD4$^+$ T cells and not on accessory cells.

Discussion

In this study we show that IL-3 is an important factor that contributes to development of the early, but not the late phase of collagen induced arthritis. Blockade of IL-3 with a monoclonal antibody during onset of arthritis markedly reduced clinical and histological signs of arthritis and the number of infiltrating cells, while blockade of IL-3 in mice with established arthritis had no effect. In the early phase of arthritis, availability of IL-3 seems to be a disease limiting factor, as application of IL-3 markedly increased the severity and incidence of arthritis. IL-3 is produced systemically by CD4+ T cells in the spleen as well as locally by cells in the synovial tissue and may aggravate early arthritis by acting systemically as well as locally within the joint. Blockade of IL-3 resulted in a significantly reduced number of basophils in the peripheral blood and reduced plasma titers of antibodies against collagen measured at the end of the α-IL-3 treatment. We have recently shown that activated basophils significantly contribute to the development of a humoral memory immune response. Activated basophils release soluble factors (mainly IL-6) and provide cell-cell contact dependent factors that promote proliferation of B cells and their differentiation into plasma cells in vitro and in vivo (22). It is tempting to speculate that IL-3 aggravates early arthritis by increasing the number of basophils in the peripheral blood, by activation of basophils and by increasing plasma titers of antibodies against collagen. We show that IL-3 is a very potent activator of basophils and markedly prolongs the survival of basophils in vitro and that application of IL-3 in vivo results in higher plasma levels of antibodies against collagen, 2-fold higher numbers of basophils in the peripheral blood and 5-fold higher IL-6 plasma levels. However, one has to keep in mind that IL-3 has also several other target cells (e.g. monocytes and dendritic cells as detailed in the introduction) that may contribute to the development of arthritis. Apart from systemic effects, IL-3 may have local effects in the joint. IL-3 is readily detectable in mildly inflamed joints (score 0-2) but is downregulated in strongly inflamed joints (score 3-4). There are again several potential target cells for IL-3 in the joints. IL-3 may increase the release of IL-1 from monocytes and may induce development of osteoclasts (14, 17). We have analyzed in more detail the presence of basophils and mast cells in the joints of mice with collagen induced arthritis and found a rather high frequency of basophils in the inflamed synovial tissue of mice with arthritis (about 0.4% of total infiltrating leukocytes), while mast cells were almost undetectable. Due to conflicting results in various models of arthritis and different strains of mast cell deficient mice, the role of mast cells for development of arthritis is currently unclear (23-25). Our data suggest that pro-arthritogenic effects of IL-3 may partially be mediated by activation of basophils and are in line with previous data showing aggravation of arthritis by application of anti-IgE or anti-CCR2 antibodies, both of which are known to activate basophils (26, 27).

To better understand why expression of IL-3 in the synovial tissue is negatively correlated with the severity of arthritis and how the expression of IL-3 is regulated, we performed in vitro assays with CD4$^+$ T cells that are considered as the main cellular source of IL-3. Apart from promoter analysis and suppression by cyclosporin A, very limited data is available on the regulation of IL-3 production by T cells (28). IL-3 expression is found in both TH1 and TH2 cells (29). We show that production of IL-3 by CD4$^+$ T cells is dependent on the level of costimulation provided to CD4$^+$ T cells. Activation of CD4$^+$ T cells with α-CD3 in the presence of freshly isolated B cells resulted in little expression of IL-3, while the presence of monocytes or B cells and monocytes activated with ligands for TLR-4 or TLR-9 markedly upregulated production of IL-3 by CD4$^+$ T cells. Using intracellular cytokine staining and cells from TLR-4 deficient C3H mice we show that LPS upregulated IL-3 production in CD4$^+$ T cells by acting on B cells but not directly on T cells. It is known that LPS aggravates, whereas blockade of TLR-4 improves collagen induced arthritis (30, 31). We also analyzed how proinflammatory cytokines present in inflamed joints modulate the secretion of IL-3 by polyclonally activated CD4$^+$ T cells and found that IL-6 and IL-4, but not IL-1β, TNF-α or MIP-2 down-regulate IL-3 expression by CD4$^+$ T cells. A combination of IL-4 and IL-6 almost completely prevented IL-3 production induced by monocytes or LPS-stimulated B cells and monocytes. As basophils produce large amounts of IL-4 and IL-6, one could postulate a negative feedback between activation of basophils and IL-3 production by T cells. Restimulation of total splenocytes and splenocytes depleted of specific leukocyte subsets with collagen type II confirmed that IL-3 is almost exclusively produced by CD4$^+$ T cells and requires the presence of antigen presenting CD11b$^+$ monocytes. B cells do not support IL-3 production by CD4$^+$ T cells in the absence of monocytes.

In summary, our data demonstrate that IL-3 is involved in the development of collagen induced arthritis and may represent a novel therapeutic target for early forms of rheumatoid arthritis or for prevention of flares in maintenance therapy.

EXAMPLE 2

The presence of IL-3 in synovial fluid or in the plasma was found to be an indicator for an active form of rheumatoid arthritis. This is shown in the following test. To analyze whether IL-3 is detectable in the synovial fluid or in the plasma of patients with arthritis, 21 patients were tested, who presented to a rheumatologist with symptoms of arthritis. From these patients plasma was obtained by a standard method. Moreover, synovial fluid was obtained by arthrocentesis and was used for the test after centrifugation.

For the determination of IL-3 both in plasma and synovial fluid an ELISA test was used. The results are shown in FIG. 7. As can be seen in 6 out of 8 patients with a diagnosis of active rheumatoid arthritis IL-3 was found in plasma or synovial fluid. Neither in patients diagnosed with non-active RA nor in patients with other type of arthritis IL-3 could be detected.

The patients were diagnosed for rheumatoid arthritis or other type of arthritis, i.e. M. Sjoegren, osteoarthritis, Stills disease or spondyl arthritis by the following test. The level of plasma C-reactive protein (CRP) and the count for leucocytes in synovial fluid were defined for active and non-active arthritis. Active RA was defined as CRP>20 mg/l or synovial fluid leucocyte count>10000/μl. Thus, 14 patients were diagnosed with rheumatoid arthritis, 8 of which were found to have active rheumatoid arthritis and 7 patients were diagnosed with another type of arthritis. In those patients with active rheumatoid arthritis the level of IL-3 in the plasma or in the synovial fluid was mean 9.5 pg/ml±3.3 sem.

These data show that IL-3 is present only in patients suffering from active forms of rheumatoid arthritis. In these cases patients can be treated by blocking IL-3 which alleviates or remedies the disease. Those patients having no detectable IL-3 level cannot be treated by the IL-3 inhibitor of the present invention.

REFERENCES

1. Miyajima A, Kitamura T, Harada N, Yokota T, Arai K. Cytokine receptors and signal transduction. Annu. Rev. Immunol. 1992; 10:295-331.
2. Hara T, Miyajima A. Two distinct functional high affinity receptors for mouse interleukin-3 (IL-3). Embo J. 1992; 11(5):1875-84.
3. Lantz C S, Boesiger J, Song C H, Mach N, Kobayashi T, Mulligan R C, et al. Role for interleukin-3 in mast-cell and basophil development and in immunity to parasites. Nature. 1998; 392(6671):90-3.
4. Ihle J N, Keller J, Oroszlan S, Henderson L E, Copeland T D, Fitch F, et al. Biologic properties of homogeneous interleukin 3.1. Demonstration of WEHI-3 growth factor activity, mast cell growth factor activity, p cell-stimulating factor activity, colony-stimulating factor activity, and histamine-producing cell-stimulating factor activity. J. Immunol. 1983; 131(1):282-7.
5. Kirshenbaum A S, Goff J P, Dreskin S C, Irani A M, Schwartz L B, Metcalfe D D. IL-3-dependent growth of basophil-like cells and mastlike cells from human bone marrow. J. Immunol. 1989; 142(7):2424-9.
6. Valent P, Schmidt G, Besemer J, Mayer P, Zenke G, Liehl E, et al. Interleukin-3 is a differentiation factor for human basophils. Blood. 1989; 73(7):1763-9.
7. Dvorak A M, Seder R A, Paul W E, Morgan E S, Galli S J. Effects of interleukin-3 with or without the c-kit ligand, stem cell factor, on the survival and cytoplasmic granule formation of mouse basophils and mast cells in vitro. Am. J. Pathol. 1994; 144(1):160-70.
8. Haak-Frendscho M, Arai N, Arai K, Baeza M L, Finn A, Kaplan A P. Human recombinant granulocyte-macrophage colony-stimulating factor and interleukin 3 cause basophil histamine release. J. Clin. Invest. 1988; 82(1):17-20.
9. MacDonald S M, Schleimer R P, Kagey-Sobotka A, Gillis S, Lichtenstein L M. Recombinant IL-3 induces histamine release from human basophils. J. Immunol. 1989; 142(10): 3527-32.
10. Kurimoto Y, de Weck A L, Dahinden C A. Interleukin 3-dependent mediator release in basophils triggered by C5a. J. Exp. Med. 1989; 170(2):467-79.
11. Le Gros G, Ben-Sasson S Z, Conrad D H, Clark-Lewis I, Finkelman F D, Plaut M, et al. IL-3 promotes production of IL-4 by splenic non-B, non-T cells in response to Fc receptor cross-linkage. J. Immunol. 1990; 145(8):2500-6.
12. Yoshimoto T, Tsutsui H, Tominaga K, Hoshino K, Okamura H, Akira S, et al. IL-18, although antiallergic when administered with IL-12, stimulates IL-4 and histamine release by basophils. Proc. Natl. Acad. Sci. USA. 1999; 96(24):13962-6.
13. Frendl G, Beller D I. Regulation of macrophage activation by IL-3.1. IL-3 functions as a macrophage-activating factor with unique properties, inducing Ia and lymphocyte function-associated antigen-1 but not cytotoxicity. J. Immunol. 1990; 144(9):3392-9.
14. Frendl G, Fenton M J, Beller D I. Regulation of macrophage activation by IL-3. II. IL-3 and lipopolysaccharide act synergistically in the regulation of IL-1 expression. J. Immunol. 1990; 144(9):3400-10.
15. Buelens C, Bartholome E J, Amraoui Z, Boutriaux M, Salmon I, Thielemans K, et al. Interleukin-3 and interferon beta cooperate to induce differentiation of monocytes into dendritic cells with potent helper T-cell stimulatory properties. Blood. 2002; 99(3):993-8.
16. Ebner S, Hofer S, Nguyen V A, Furhapter C, Herold M, Fritsch P, et al. A novel role for IL-3: human monocytes cultured in the presence of IL-3 and IL-4 differentiate into dendritic cells that produce less IL-12 and shift Th cell responses toward a Th2 cytokine pattern. J. Immunol. 2002; 168(12):6199-207.

17. Barton B E, Mayer R. IL-3 induces differentiation of bone marrow precursor cells to osteoclast-like cells. J. Immunol. 1989; 143(10):3211-6.
18. Toyosaki-Maeda T, Takano H, Tomita T, Tsuruta Y, Maeda-Tanimura M, Shimaoka Y, et al. Differentiation of monocytes into multinucleated giant bone-resorbing cells: two-step differentiation induced by nurse-like cells and cytokines. Arthritis Res. 2001; 3(5):306-10.
19. Firestein G S, Xu W D, Townsend K, Broide D, Alvaro-Gracia J, Glasebrook A, et al. Cytokines in chronic inflammatory arthritis. I. Failure to detect T cell lymphokines (interleukin 2 and interleukin 3) and presence of macrophage colony-stimulating factor (CSF-1) and a novel mast cell growth factor in rheumatoid synovitis. J. Exp. Med. 1988; 168(5):1573-86.
20. Alvaro-Gracia J M, Zvaifler N J, Firestein G S. Cytokines in chronic inflammatory arthritis. V. Mutual antagonism between interferon-gamma and tumor necrosis factor-alpha on HLA-DR expression, proliferation, collagenase production, and granulocyte macrophage colony-stimulating factor production by rheumatoid arthritis synoviocytes. J. Clin. Invest. 1990; 86(6):1790-8.
21. Yamada R, Tanaka T, Unoki M, Nagai T, Sawada T, Ohnishi Y, et al. Association between a single-nucleotide polymorphism in the promoter of the human interleukin-3 gene and rheumatoid arthritis in Japanese patients, and maximum-likelihood estimation of combinatorial effect that two genetic loci have on susceptibility to the disease. Am. J. Hum. Genet. 2001; 68(3):674-85.
22. Denzel A, Maus U A, Gomez M R, Moll C, Niedermeier M, Winter C, et al. Basophils enhance immunological memory responses. Nat. Immunol. 2008; 9(7):733-42.
23. Lee D M, Friend D S, Gurish M F, Benoist C, Mathis D, Brenner M B. Mast cells: a cellular link between autoantibodies and inflammatory arthritis. Science. 2002; 297(5587):1689-92.
24. Nigrovic P A, Binstadt B A, Monach P A, Johnsen A, Gurish M, Iwakura Y, et al. Mast cells contribute to initiation of autoantibody-mediated arthritis via IL-1. Proc. Natl. Acad. Sci. USA. 2007; 104(7):2325-30.
25. Zhou J S, Xing W, Friend D S, Austen K F, Katz H R. Mast cell deficiency in Kit(W-sh) mice does not impair antibody-mediated arthritis. J. Exp. Med. 2007; 204(12):2797-802.
26. Bruhl H, Cihak J, Plachy J, Kunz-Schughart L, Niedermeier M, Denzel A, et al. Targeting of Gr-1+, CCR2+ monocytes in collagen-induced arthritis. Arthritis Rheum. 2007; 56(9):2975-85.
27. Bruhl H, Cihak J, Schneider M A, Plachy J, Rupp T, Wenzel I, et al. Dual role of CCR2 during initiation and progression of collagen-induced arthritis: evidence for regulatory activity of CCR2+ T cells. J. Immunol. 2004; 172(2):890-8.
28. Hawwari A, Burrows J, Vadas M A, Cockerill P N. The human IL-3 locus is regulated cooperatively by two NFAT-dependent enhancers that have distinct tissue-specific activities. J. Immunol. 2002; 169(4):1876-86.
29. Stevens T L, Bossie A, Sanders V M, Fernandez-Botran R, Coffman R L, Mosmann T R, et al. Regulation of antibody isotype secretion by subsets of antigen-specific helper T cells. Nature. 1988; 334(6179):255-8.
30. Yoshino S, Sasatomi E, Mori Y, Sagai M. Oral administration of lipopolysaccharide exacerbates collagen-induced arthritis in mice. J. Immunol. 1999; 163(6):3417-22.
31. Abdollahi-Roodsaz S, Joosten L A, Roelofs M F, Radstake T R, Matera G, Popa C, et al. Inhibition of Toll-like receptor 4 breaks the inflammatory loop in auto-immune destructive arthritis. Arthritis Rheum. 2007; 56(9):2957-67.
32. Emanuel P D, Peiper S C, Chen Z, Sheng D C, Zuckerman K S. Specific inhibition of interleukin 3 bioactivity by a monoclonal antibody reactive with hematopoietic progenitor cells. Proc Natl Acad Sci USA. 1990 June; 87(12): 4449-52.
33. Sun Q, Woodcock J M, Rapoport A, Stomski F C, Korpelainen E I, Bagley C J, Goodall G J, Smith W B, Gamble J R, Vadas M A, Lopez A F. Monoclonal antibody 7G3 recognizes the N-terminal domain of the human interleukin-3 (IL-3) receptor alpha-chain and functions as a specific IL-3 receptor antagonist. Blood. 1996 Jan. 1; 87(1): 83-92.
34. Watanabe Y, Kitamura T, Hayashida K, Miyajima A. Monoclonal antibody against the common beta subunit (beta c) of the human interleukin-3 (IL-3), IL-5, and granulocyte-macrophage colony-stimulating factor receptors shows upregulation of beta c by IL-1 and tumor necrosis factor-alpha. Blood. 1992 Nov. 1; 80(9):2215-20.
35. Morel P A, Schreurs J, Townsend K, Gross M, Chiller J M, Tweardy D J. Identification of a novel protein capable of interacting with the IL-3 receptor. J Immunol. 1991 Apr. 1; 146(7):2295-304.
36. Ellington A D, Szostak J W: In vitro selection of RNA molecules that bind specific ligands. Nature 1990, 346: 818-822
37. Tuerk C, Gold L: Systematic evolution of ligands by exponential enrichment: RNA ligands to bacteriophage T4 DNA polymerase. Science 1990, 249:505-510
38. Klussmann S, Nolte A, Bald R, Erdmann V A, Furste J P: Mirror-image RNA that binds D-adenosine. Nat Biotechnol 1996, 14:1112-1115.

The invention claimed is:

1. A method of treating rheumatoid arthritis (RA) in a subject, comprising administering an anti-IL-3 antibody to the subject that selectively binds to IL-3, wherein the subject has early stage rheumatoid arthritis, or is in early phase of rheumatoid arthritis exacerbation, and wherein the subject has a disease activity score 28 (DAS28) of up to 5.1, and wherein the anti-IL-3 antibody decreases plasma IL-6 level.

2. The method of claim 1, wherein an increased level of IL-3 in one or more joints is detectable.

3. The method of claim 1, wherein the subject has a DAS28 score of up to 3.2.

4. The method of claim 1, wherein the anti-IL-3 antibody reduces progression of rheumatoid arthritis.

5. The method of claim 1, wherein the anti-IL-3 antibody reduces cartilage destruction.

6. The method of claim 1, wherein the anti-IL-3 antibody reduces cell infiltration of synovial tissue.

7. The method of claim 1, wherein the anti-IL-3 antibody decreases the number of basophils.

8. The method of claim 1, wherein the subject is a mammal, particularly a human.

9. The method of claim 1 wherein the anti-IL-3 antibody is a monoclonal, polyclonal, chimeric antibody or a fragment thereof.

10. The method of claim 9, wherein the anti-IL-3 antibody is a human or humanized antibody.

11. The method of claim 1, wherein the anti-IL-3 antibody does not bind with other cytokines.

12. The method of claim 1 wherein the anti-IL-3 antibody is administered with a pharmaceutically acceptable carrier and wherein the anti-IL3 antibody is at a concentration that neutralizes IL-3 bioactivity.

13. The method of claim 12, wherein a neutralization dose$_{50}$ of the anti-IL-3 antibody is administered.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
tccatgacgt tcctgatgct                                           20